US012312325B2

(12) United States Patent
Chen et al.

(10) Patent No.: US 12,312,325 B2
(45) Date of Patent: May 27, 2025

(54) METHODS AND COMPOUNDS USEFUL IN THE SYNTHESIS OF AN AAK1 INHIBITOR

(71) Applicant: Lexicon Pharmaceuticals, Inc., The Woodlands, TX (US)

(72) Inventors: Tao Chen, Wuxi (CN); Wenxue Wu, Princeton Junction, NJ (US); Jun Yan, Changzhou (CN); Xianglu Zeng, Changzhou (CN); Matthew Mangzhu Zhao, Edison, NJ (US)

(73) Assignee: LEXICON PHARMACEUTICALS, INC., The Woodlands, TX (US)

(*) Notice: Subject to any disclaimer, the term of this patent is extended or adjusted under 35 U.S.C. 154(b) by 155 days.

(21) Appl. No.: 18/114,050

(22) Filed: Feb. 24, 2023

(65) Prior Publication Data

US 2023/0357181 A1    Nov. 9, 2023

Related U.S. Application Data

(60) Provisional application No. 63/315,504, filed on Mar. 1, 2022.

(51) Int. Cl.
| | |
|---|---|
| C07D 213/65 | (2006.01) |
| B01J 31/22 | (2006.01) |
| C07C 63/06 | (2006.01) |
| C07C 63/08 | (2006.01) |
| C07C 215/08 | (2006.01) |
| C07D 213/61 | (2006.01) |
| C07D 401/04 | (2006.01) |

(52) U.S. Cl.
CPC ........ C07D 401/04 (2013.01); B01J 31/2295 (2013.01); B01J 2531/824 (2013.01)

(58) Field of Classification Search
CPC ................ C07D 401/04; B01J 31/2295; B01J 2531/824
See application file for complete search history.

(56) References Cited

U.S. PATENT DOCUMENTS

| 9,902,722 B2 * | 2/2018 | Luo ...................... C07D 239/26 |
| 2018/0346440 A1 * | 12/2018 | Bronson ................ A61P 25/16 |
| 2024/0343720 A1 * | 10/2024 | Li ........................ C07D 213/74 |

FOREIGN PATENT DOCUMENTS

| WO | 2017059085 A1 | 4/2017 |
| WO | 2021216441 A1 | 10/2021 |
| WO | WO-2023051749 A1 * | 4/2023 |

OTHER PUBLICATIONS

Bastin et al. "Salt Selection and Optimisation Procedures for Pharmaceutical New Chemical Entities." Organic Process Research & Development (2000), 4, 427-435 (Year: 2000).*

Hilfiker et al. "Relevance of Solid-state Properties for Pharmaceutical Products." Wiley (2006), 1-19 (Year: 2006).*

Thackaberry (Thackaberry, Evan. "Non-clinical toxicological considerations for pharmaceutical salt selection." Expert Opinion on Drug Metabolism & Toxicology (2012), 8:11, 1419-1433) (Year: 2012).*

U.S. Appl. No. 18/114,104.

Boge, M , et al., "A Membrane-proximal Tyrosine-based Signal Mediates Internalization of the HIV-1 Envelope Glycoprotein via Interaction with the AP-2 Clathrin Adaptor", J Biol Chem 273, 15773-15778 (1998).

Buonanno, A , "The Neuregulin Signaling Pathway and Schizophrenia: From Genes to Synapses and Neural Circuits", Brain Res Bull 83, 122-131 (2010).

Caira, M. , et al., "Crystalline Polymorphism of Organic Compounds", Topics in Current Chemistry, vol. 198, 163-208 (1998).

Conner, S , et al., "AAK1-Mediated m2 Phosphorylation is Stimulated by Assembled Clathrin", Traffic 4, 885-890 (2003).

Conner, S , et al., "Skip Nav Destination Article|Mar. 4, 2002 Identification of an adaptor-associated kinase, AAK1, as a regulator of clathrin-mediated endocytosis", J Cell Bio 156, 921-929 (2002).

Greenwood, T , et al., "Analysis of 94 candidate genes and 12 endophenotypes for schizophrenia from the Consortium on the Genetics of Schizophrenia", Am J Psychiatry 168, 930-946 (2011).

Hartz, R , et al., "Discovery, Structure-Activity Relationships, and In Vivo Evaluation of Novel Aryl Amides as Brain Penetrant Adaptor Protein 2-Associated Kinase 1 (AAK1) Inhibitors for the Treatment of Neuropathic Pain", J Med Chem 64 (15), 11090-11128 (2021).

Henderson , et al., "A Novel AAK1 Splice Variant Functions at Multiple Steps of the Endocytic Pathway", Mol Biol Cell 18, 2698-2706 (2007).

Hilfiker, R , "Polymorphism in the Pharmaceutical Industry", ISBN: 978-4-637-42257-0, pp. 1-19 (2006).

Jaaro-Peled, H , et al., "Review of Pathological Hallmarks of Schizophrenia: Comparison of Genetic Models With Patients and Nongenetic Models", Schizophrenia Bulletin 36, 301-313 (2010).

Kuai, L , et al., "AAK1 Identified as an Inhibitor of Neuregulin-1/ErbB4-Dependent Neurotrophic Factor Signaling Using Integrative Chemical Genomics and Proteomics", Chemistry and Biology 18, 891-906 (2011).

Latourelle, J , et al., "Genomewide association study for onset age in Parkinson disease", BMC Med Genet 10, 98, doi: 10.1186/1471-2350-10-98 (2009).

Motely, A, et al., "Functional Analysis of AP-2 α and µ2 Subunits", Mol Biol Cell 17, 5298-5308 (2006).

Neveu, G , et al., "AP-2-associated protein kinase 1 and cyclin G-associated kinase regulate hepatitis C virus entry and are potential drug targets", J Virol 89 (8), 4387-4404 (2015).

Neveu, G , et al., "Identification and Targeting of an Interaction between a Tyrosine Motif within Hepatitis C Virus Core Protein and AP2M1 Essential for Viral Assembly", PLoS Pathog 8, 1-16, e1002845.doi: 10.1371/journal.ppat.1002845 (2012).

(Continued)

*Primary Examiner* — Kortney L. Klinkel
*Assistant Examiner* — Alison Azar Salamatian
(74) *Attorney, Agent, or Firm* — Viksnins Harris Padys Malen LLP

(57) ABSTRACT

Methods for the synthesis of (S)-1-((2',6-bis(difluoromethyl)-[2,4'-bipyridin]-5-yl)oxy)-2,4-dimethylpentan-2-amine and salts thereof are disclosed, as well as compounds useful therein.

16 Claims, 2 Drawing Sheets

(56) References Cited

OTHER PUBLICATIONS

Figure 1:
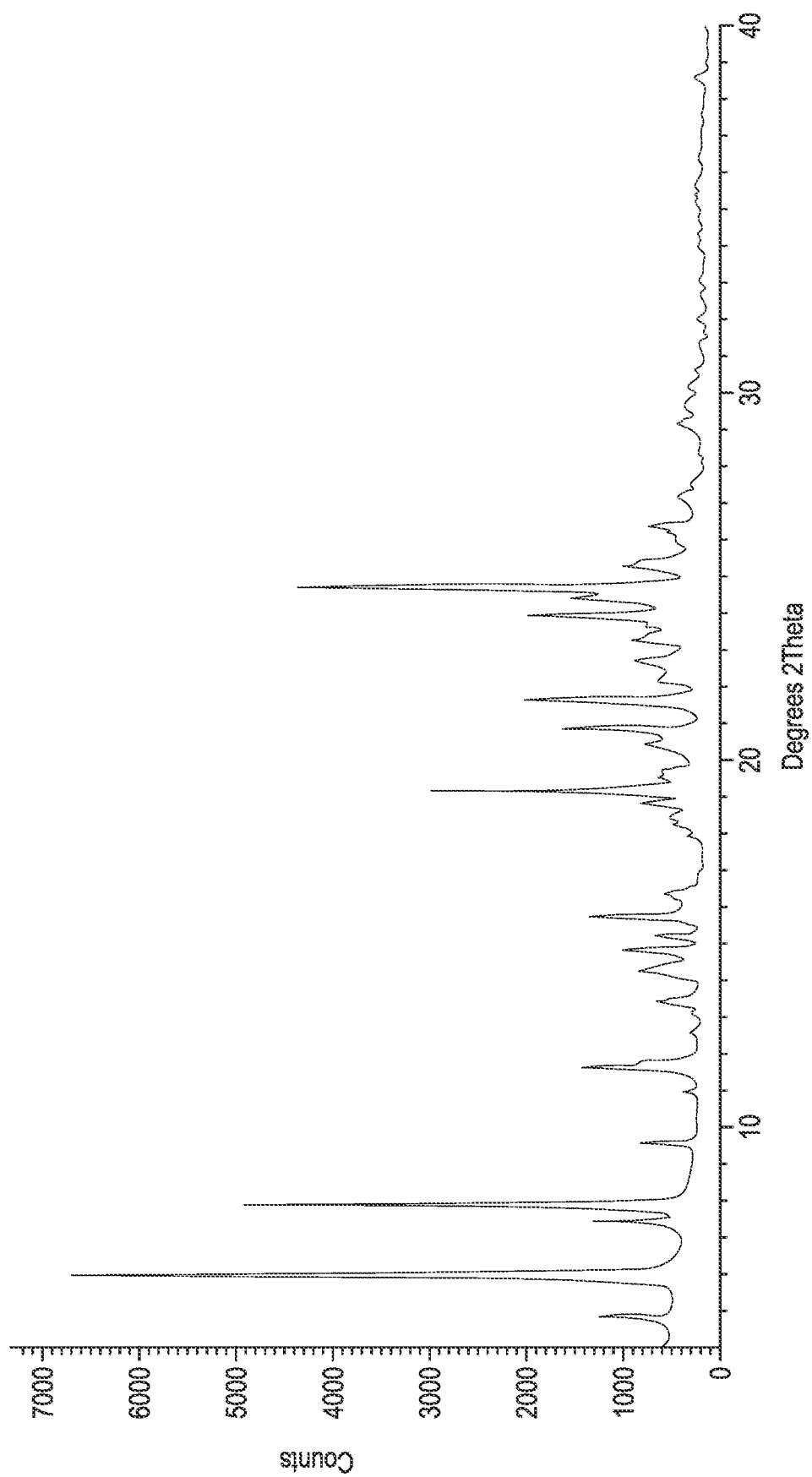

Patent Cooperation Treaty, International Search Report and Written Opinion for PCT/US2023/013840, 17 pages dated Jul. 28, 2023.
Ricotta, D, et al., "Phosphorylation of the AP2 u subunit by AAK1 mediates high affinity binding to membrane protein sorting signals", J Cell Bio 156, 791-795 (2002).
Thackaberry, E, "Non-clinical toxicological considerations for pharmaceutical salt selection", Expert Opinion on Drug Metabolism & Toxicology 8(11), 1419-1433 (2012).
Wen, L, et al., "Neuregulin 1 regulates pyramidal neuron activity via ErbB4 in parvalbumin-positive interneurons", Proc Natl Acad Sci 107, 1211-1216 (2010).
Luo, G, et al., "Discovery of (S)-1-((2',6-Bis(difluoromethyl)-[2,4'-bipyridin]-5-yl)oxy)-2,4-dimethylpentan-2-amine (BMS-986176/LX-9211): A Highly Selective, CNS Penetrable, and Orally Active Adaptor Protein-2 Associated Kinase 1 Inhibitor in Clinical Trials for the Treat", J Med Chem 65, 4457-4480 (2022).

* cited by examiner

METHODS AND COMPOUNDS USEFUL IN THE SYNTHESIS OF AN AAK1 INHIBITOR

1 FIELD OF THE INVENTION

This application relates to methods of making (S)-1-((2',6-bis(difluoromethyl)[2,4'-bipyridin]-5-yl)oxy)-2,4-dimethylpentan-2-amine and salt forms thereof, and to synthetic intermediates useful therein.

2 BACKGROUND OF THE INVENTION

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clathrin coated endocytosis, a process that is important in synaptic vesicle recycling and receptor-mediated endocytosis. AAK1 associates with the AP2 complex, which links receptor cargo to the clathrin coat. The binding of clathrin to AAK1 stimulates AAK1 kinase activity (Conner et al., *Traffic* 2003, 4, 885-890; Jackson et al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et al., *Am. J. Psychiatry* 2011, 168, 930-946). Neuregulin 1 and ErbB4 KO mouse models have shown schizophrenia relevant morphological changes and behavioral phenotypes (Jaaro-Peled et al., *Schizophrenia Bulletin* 2010, 36, 301-313; Wen et al., *Proc. Natl. Acad. Sci. USA.* 2010, 107, 1211-1216). In addition, a single nucleotide polymorphism in an intron of the AAK1 gene has been associated with the age of onset of Parkinson's disease (Latourelle et al., *BMC Med. Genet.* 2009, 10, 98). These results suggest that inhibition of AAK1 activity may have utility in the treatment of schizophrenia, cognitive deficits in schizophrenia, Parkinson's disease, neuropathic pain, bipolar disorder, and Alzheimer's disease.

In addition, studies using Huh-7.5 cells indicate a potential utility for AAK1 kinase inhibitors in the treatment of hepatitis C (HCV) infection. Reduction of AAK1 protein using RNA interference mediated gene silencing, treatment with the kinase inhibitor sunitinib (a potent AAK1 inhibitor), and overexpression of Mu2 (AAK1 substrate) phosphorylation site mutant all result in reduced HCV virion assembly. Furthermore, the same treatments were shown to inhibit HCV entry, suggesting AAK1 inhibitors can disrupt two host dependent stages of the virus life cycle (Neveu et al., *PLoS Pathog.* 2012, 8, 1-16; Neveu et al., *J. Virol.* 2015, posted online 4 February). AAK1 inhibitors may also be useful against HIV and HBV (See, e.g., Boge et al., *J. Biol. Chem.* 1998, 273, 15773-15778).

A number of AAK1 inhibitors have disclosed in the literature, and it has been suggested that some may be useful in the treatment of neuropathic pain. See, e.g., Hartz, R. A., et al., *J. Med. Chem.*, 2021 Aug. 12; 64(15):11090-11128. However, human clinical trials are necessary to evaluation the full potential of any drug.

The specific AAK1 inhibitor (S)-1-((2',6-bis(difluoromethyl)-[2,4'-bipyridin]-5-yl)oxy)-2,4-dimethylpentan-2-amine has been prepared on a small, laboratory scale. See, e.g., U.S. Pat. No. 9,902,722. Unfortunately, synthetic approaches useful in the laboratory setting are rarely suitable for large-scale manufacture of pharmaceutically acceptable material. For example, the creation of potentially harmful reaction byproducts needs to be minimized, and the use of toxic solvents and reagents are preferably avoided. Moreover, reaction conditions that may work on a gram scale are often inefficient or even dangerous when scaled up. Consequently, a need exists for synthetic methods that can be used to prepare pharmaceutically acceptable (S)-1-((2',6-bis(difluoromethyl)[2,4'-bipyridin]-5-yl)oxy)-2,4-dimethylpentan-2-amine in commercially useful quantities.

3 SUMMARY OF THE INVENTION

This application is directed to methods of making the compound (S)-1-((2',6-bis(difluoromethyl)[2,4'-bipyridin]-5-yl)oxy)-2,4-dimethylpentan-2-amine (Compound J):

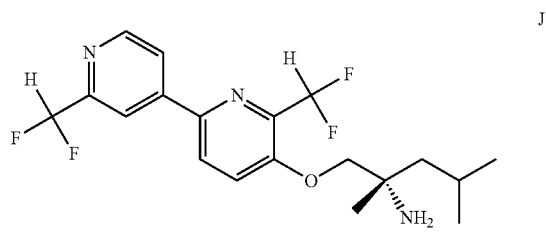 [SMILES: CC(C)C[C@](C)(N)COc1ccc(-c2ccnc(C(F)F)c2)nc1C(F)F]

and salts thereof. Compound J is an inhibitor of adaptor associated kinase 1 (AAK1) and is believed to be useful in the treatment of diseases and disorders including pain.

In one embodiment, this invention encompasses a method of preparing (S)-1-((2',6-bis(difluoromethyl)-[2,4'-bipyridin]-5-yl)oxy)-2,4-dimethylpentan-2-amine (Compound J):

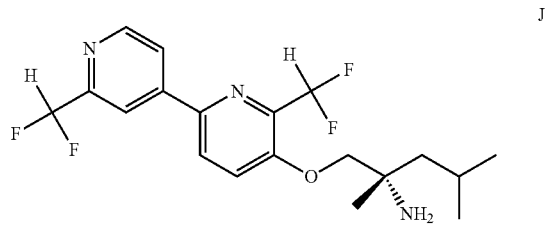 [SMILES: CC(C)C[C@](C)(N)COc1ccc(-c2ccnc(C(F)F)c2)nc1C(F)F]

which comprises contacting Compound H:

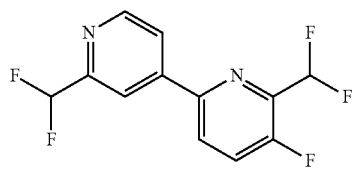

H with Compound D:

D or a salt thereof in the presence of a base under conditions sufficient to form Compound J.

In one embodiment, Compound H is prepared by contacting Compound Q:

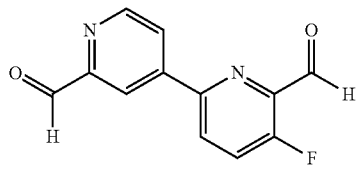

Q with a fluorinating agent under conditions sufficient to form Compound H. (This invention encompasses crystalline forms of Compound Q. A particular crystalline form has a melting point of about 150° C.)

In one embodiment, Compound Q is prepared by contacting Compound P:

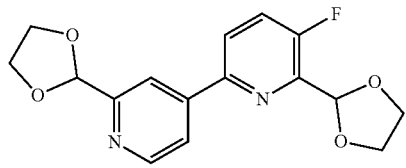

P with an acid under conditions sufficient to form Compound Q.

In one embodiment, Compound P is prepared by contacting Compound L:

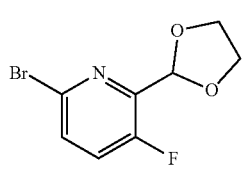

L with Compound N:

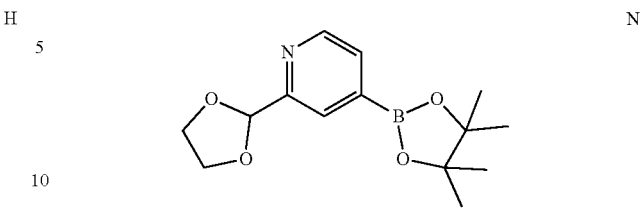

N under conditions sufficient to form Compound P.

In one embodiment, Compound Q is prepared by contacting Compound L4:

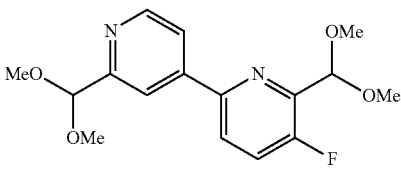

L4 with an acid under conditions sufficient to form Compound Q.

In one embodiment, Compound L4 is prepared by contacting Compound L3:

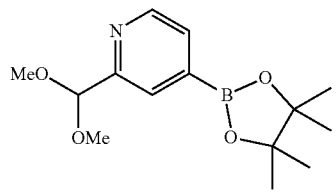

L3 with Compound L1:

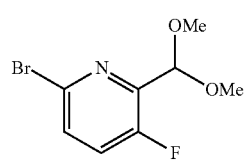

L1 in the presence of a catalyst and a base under conditions sufficient to form Compound L4.

This invention also encompasses a method of preparing Compound K:

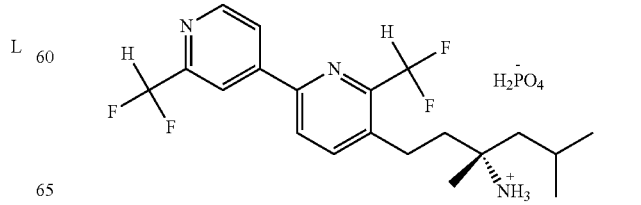

K which comprises contacting Compound S:

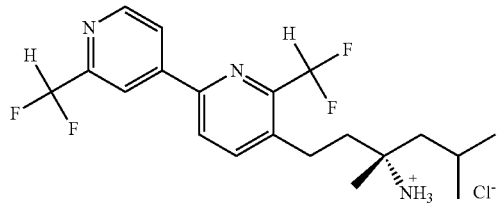

with phosphoric acid in a solvent under conditions sufficient to form Compound K.

In one embodiment, Compound S is prepared by contacting Compound J:

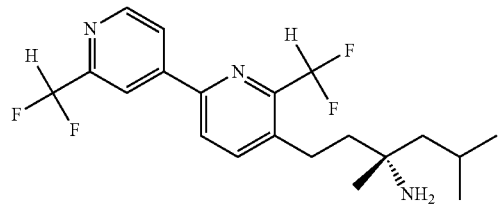

with hydrochloric acid in a solvent under conditions sufficient to form Compound S.

This invention also encompasses the synthetic intermediate 6-bromo-2-(dimethoxymethyl)-3-fluoropyridine (Compound L1):

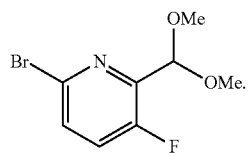

This invention also encompasses 2',6-bis(dimethoxymethyl)-5-fluoro-2,4'-bipyridine (Compound L4):

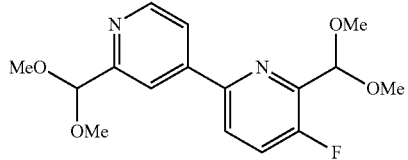

and salts thereof.

This invention also encompasses the compound 5-fluoro-[2,4'-bipyridine]-2',6-dicarbaldehyde (Compound Q):

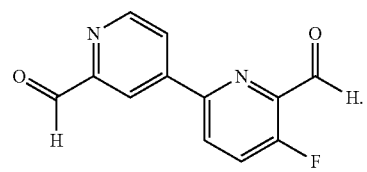

This invention also encompasses a crystalline pharmaceutically acceptable salt of (S)-1-((2',6-bis(difluoromethyl)-[2,4'-bipyridin]-5-yl)oxy)-2,4-dimethylpentan-2-amine (Compound J):

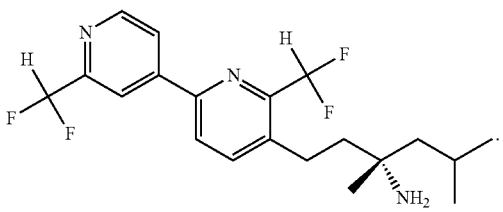

This invention also encompasses a method of determining the purity of a sample of (S)-1-((2',6-bis(difluoromethyl)-[2,4'-bipyridin]-5-yl)oxy)-2,4-dimethylpentan-2-amine (Compound J):

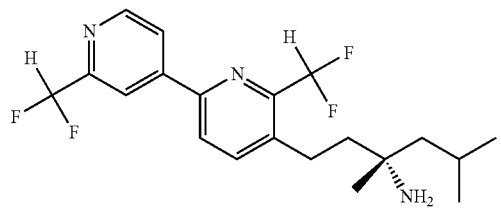

or a pharmaceutically acceptable salt thereof, which comprises testing the sample for the presence of one or more of the compounds listed in Table 1.

This invention also encompasses a composition comprising (S)-1-((2',6-bis(difluoromethyl)[2,4'-bipyridin]-5-yl)oxy)-2,4-dimethylpentan-2-amine (Compound J):

This invention also encompasses 2-(dimethoxymethyl)-4-(4,4,5,5-tetramethyl-1,3,2-dioxaborolan-2-yl)pyridine (Compound L3):

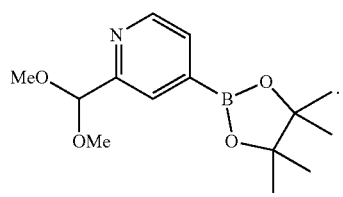

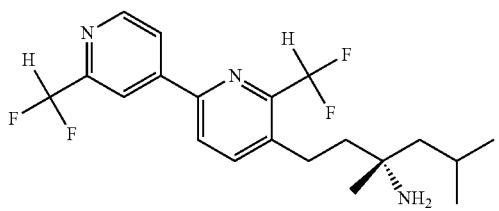

J

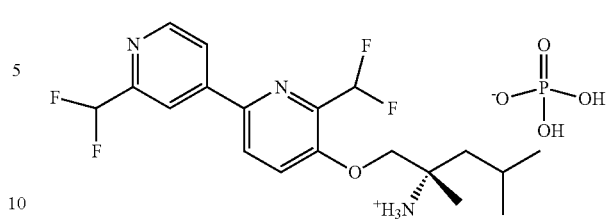

K or a pharmaceutically acceptable salt thereof, which composition comprises less than 0.01 percent by weight of one or more of the compounds listed in Table 1, below.

4 BRIEF DESCRIPTION OF THE DRAWINGS

FIG. 1 provides a representative X-ray powder diffraction (XRPD) pattern of crystalline solid form I of ((S)-1-((2',6-bis(difluoromethyl)[2,4'-bipyridin]-5-yl)oxy)-2,4-dimethyl-pentan-2-aminium dihydrogen phosphate (Compound K). The spectrum was obtained using a Bruker X-ray diffractometer with a LYNXEYE detector (copper Kα radiation).

Figure 2:
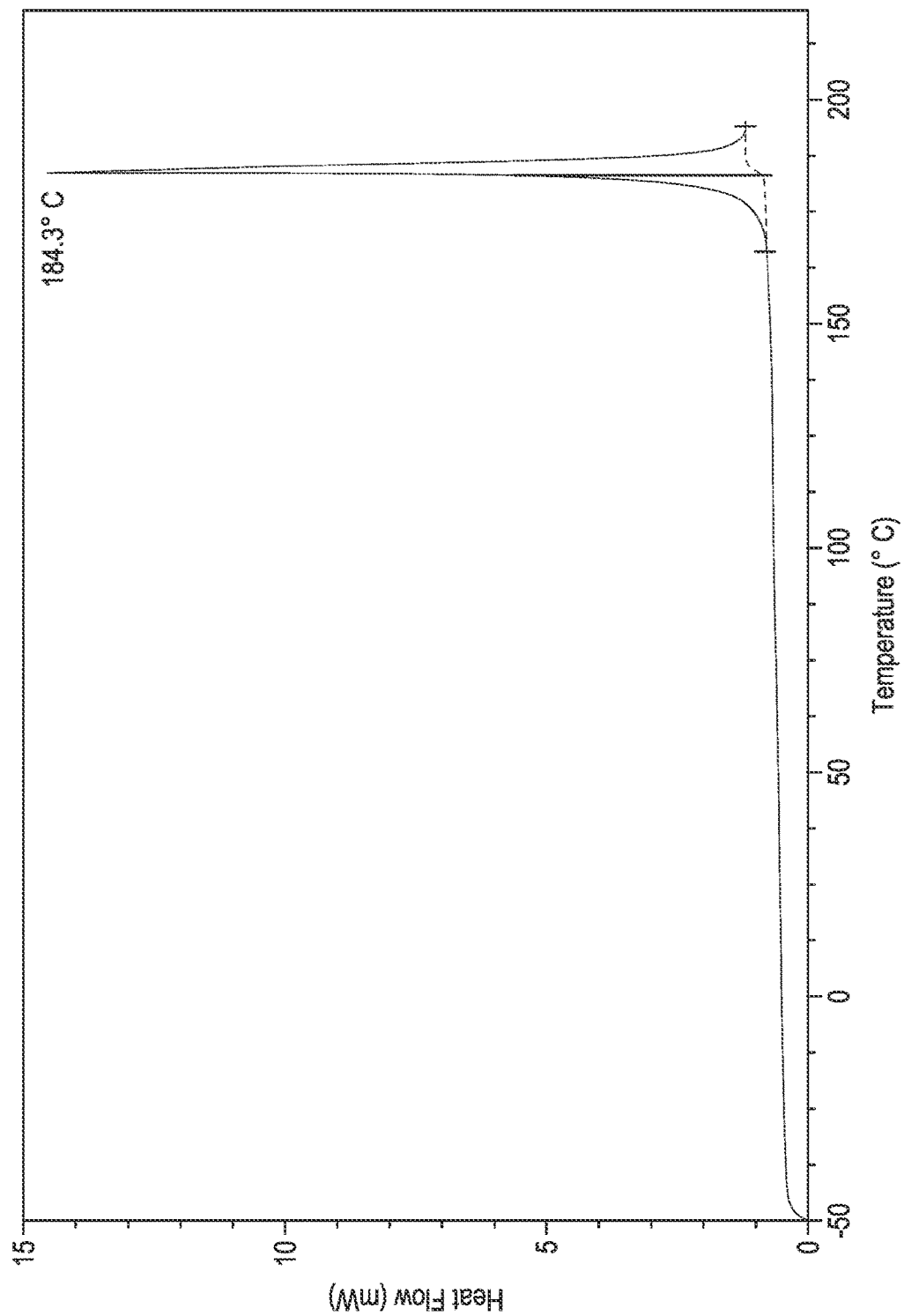

FIG. 2 provides a representative differential scanning calorimetry (DSC) thermogram of a crystalline solid form of Compound K. The thermogram was obtained using a TA Instruments DSC Q2000 instrument and a hermetically sealed gold crucible filled under ambient conditions. Two scans were performed. After the melting was completed in the first scan, the sample was rapidly cooled at approximately −40 K per minute to −50° C., and a second scan was recorded. The heating rate was 10 K per minute in both scans.

5 DETAILED DESCRIPTION

This invention is directed to synthetic intermediates and synthetic methods for the preparation of (S)-1-((2',6-bis (difluoromethyl)[2,4'-bipyridin]-5-yl)oxy)-2,4-dimethyl-pentan-2-amine (Compound J):

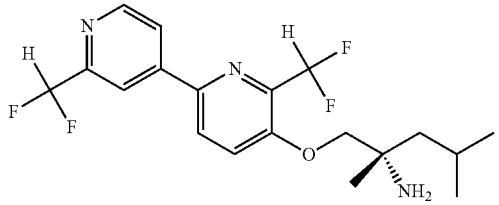

J and pharmaceutically acceptable salts thereof in quantities (e.g., greater than 1 kg, 5 kg, or 10 kg) sufficient for the manufacture of dosage forms suitable for use in human clinical trials and subsequent commercialization. Methods of this invention minimize the formation of harmful impurities while maximizing synthetic yields.

Particular methods of this invention are used to prepare ((S)-1-((2',6-bis(difluoromethyl)-[2,4'-bipyridin]-5-yl)oxy)-2,4-dimethylpentan-2-aminium dihydrogen phosphate (Compound K):

and crystalline solid forms thereof. A particular crystalline form of this salt, referred to herein as Form I, has an XRPD spectrum substantially the same as that shown in FIG. 1, with diffraction peaks at one or more of about 4.81, 5.99, 7.44, 7.89, 11.66, 14.85, 15.77, 19.19, 20.86, 21.65, 23.96, 24.48, or 24.73 degrees 2-theta. When used herein to refer to XPRD peaks, the term "about" means ±0.2 degrees 2-theta.

Crystalline Form I of Compound K has a melting point of about 184° C. (see FIG. 2) as determined by differential scanning calorimetry (DSC) (melting endotherm). When referring to a temperature, the terms "substantially" and "about" mean ±2° C.

Crystalline Form I of Compound K is the most stable of the forms discovered for this salt: neither the form itself, its morphology, nor its purity changed after having been stored at 40° C. and 75% relative humidity for up to four weeks. Moreover, while Form I has a lower melting point than a hydrochloride salt of Compound J (a form of which was found to have a melting point of about 247° C.), the phosphate salt does not show evidence of concomitant degradation. Instead, the melting of Form I is observed to recrystallize to another, metastable form having a melting point of about 172.5° C. The large-scale manufacture and purification of Form I are further aided by its water solubility, which is 26.8 mg/mL at 25° C. By comparison, a hydrochloride salt of Compound J had a measured aqueous solubility of 2.9 mg/mL at 25° C.

One embodiment of the invention, which can be used to prepare Form I, is shown below:

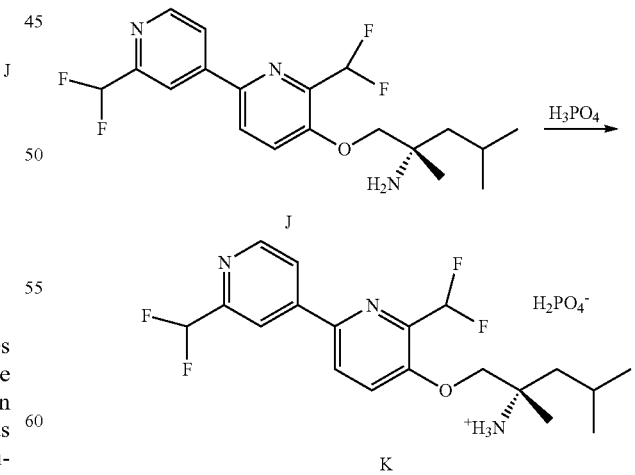

Here, Compound K is prepared by contacting Compound J with phosphoric acid in a solvent under conditions sufficient to form Compound K. Examples of solvents include water, methanol, ethanol, n-butanol, isopropanol, isobutanol, t-butanol, methyl t-butyl ether, ethyl acetate, isopropyl acetate, THF and 2-methyl THF, and mixtures thereof. A particular solvent is isopropanol.

In some embodiments, Compound J is contacted with phosphoric acid at a temperature of from about 0° C. to about 100° C. or from about 50° C. to about 60° C. (When referring to reaction conditions, the term "about" when used to refer to temperature may be construed as ±10° C. unless otherwise indicated.) In some embodiments, Compound J is contacted with phosphoric acid for about 0.5 hours to about 24 hours or for about 2 hours to about 16 hours. (When referring to reaction conditions, the term "about" when referring to time may be construed as ±5 percent unless otherwise indicated. For example, "about 2 hours" is the same as 2 hours±6 minutes.) In some embodiments, from about 0.8 to about 1.2 molar equivalents (e.g., about 1 molar equivalent) of the phosphoric acid is utilized relative to Compound J. (Unless otherwise indicated, the term "about" when referring to molar equivalents or concentration may be construed as ±5 percent.) In some embodiments, the concentration of Compound J in the solvent is from about 2% to about 25%.

In one embodiment of the invention, Compound K is prepared from Compound S as shown below:

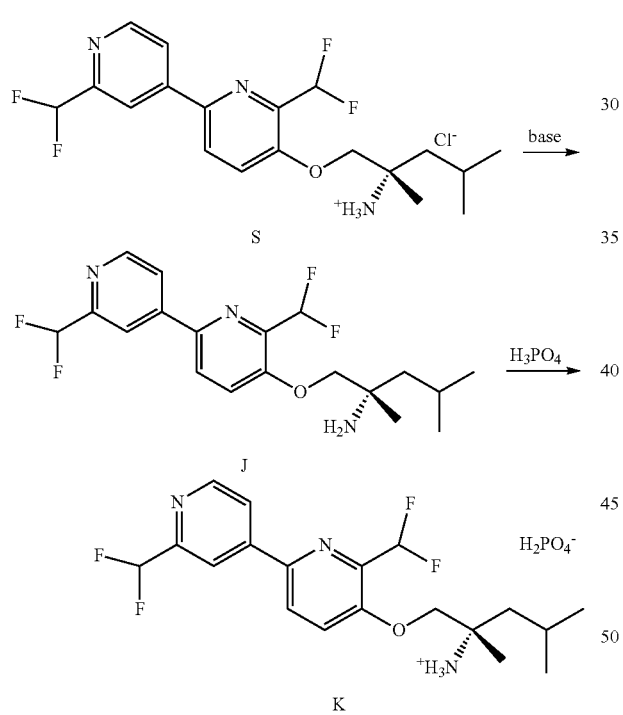

In this approach, Compound S is neutralized with a base under conditions sufficient to form Compound J, which is contacted with phosphoric acid under conditions sufficient to form Compound K. Suitable bases for the neutralization include NaOH, KOH, Na$_2$CO$_3$, and K$_2$CO$_3$. A preferred base is sodium hydroxide.

The neutralization of Compound S with a base is typically carried out in a solvent such as water, water/MTBE, water/THF and water/2-MeTHF (a preferred solvent is water/MTBE), and at a temperature of from about 0° C. to about 60° C. (e.g., from about 20° C. to about 40° C.). In some embodiments, the neutralization is carried out for about 0.5 hours to about 24 hours (e.g., for about 1 hour to about 2 hours.) In some embodiments, from about 0.8 to about 5 molar equivalents of the base is utilized relative to Compound S. In some embodiments, the concentration of Compound S in the solvent is from about 2% to about 25%.

The exposure of Compound J to phosphoric acid in the second step shown above is typically carried out in a solvent such as water, methanol, ethanol, n-butanol, isopropanol, isobutanol, t-butanol, methyl t-butyl ether, ethyl acetate, isopropyl acetate, THF and 2-methyl THF, or mixtures thereof. A preferred solvent is isopropanol.

In some embodiments, the exposure of Compound J to phosphoric acid is carried out at a temperature of from about 0° C. to about 100° C. (e.g., from about 50° C. to about 60° C.) In some embodiments, the exposure of Compound J to phosphoric acid is carried out for about 0.5 hours to about 24 hours (e.g., about seven hours to about 14 hours.) In some embodiments, from about 0.8 to about 1.2 molar equivalents of the phosphoric acid is utilized relative to Compound J in step 2. In some embodiments, the concentration of Compound J in the solvent is from about 2% to about 25%.

Compound S can be prepared as shown below:

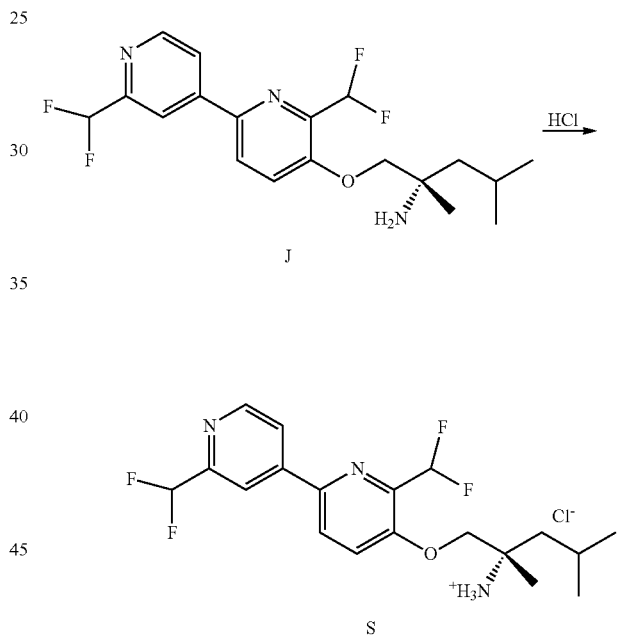

In one embodiment, Compound S is prepared by exposing Compound J to hydrochloric acid in a solvent under conditions sufficient to form Compound S. In some embodiments, the solvent is water, IPA, water/IPA mixture, MeOH, MeOH/water, EtOH, EtOH/water, n-BuOH or n-BuOH/water. A preferred solvent is isopropanol.

The exposure of Compound J to hydrochloric acid is carried out at a temperature of from about 0° C. to about 60° C. (e.g., from about 50° C. to about 60° C.) for about 0.5 hours to about 24 hours (e.g., about 4 hours to about 8 hours.) From about 0.8 to about 1.2 molar equivalents of the hydrochloric acid is typically used relative to Compound J. In some embodiments, the concentration of Compound J in the solvent is from about 2% to about 25%.

One embodiment of the invention encompasses the method of preparing Compound J shown below:

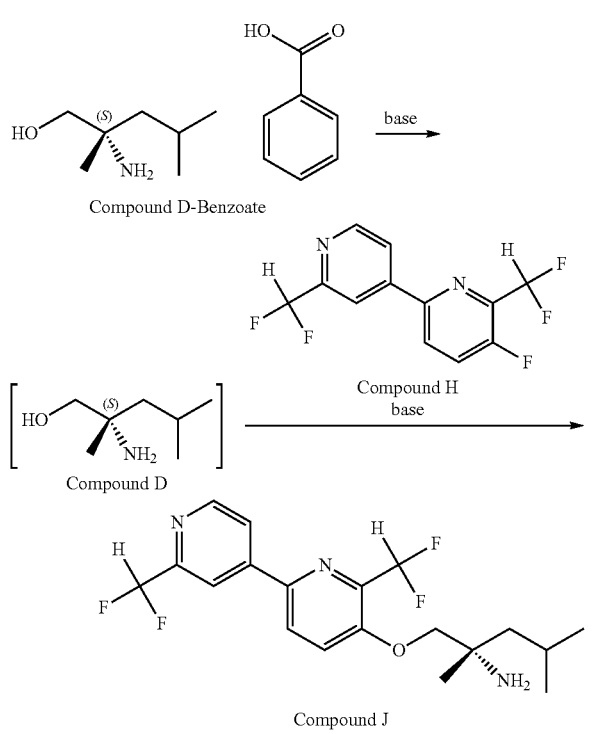

Here, Compound J is prepared by neutralizing Compound D-benzoate with a base under conditions sufficient to form Compound D, which is contacted with Compound H in the presence of a base under conditions sufficient to form Compound J. Compound D need not be isolated.

Solvents suitable for use in these reactions include THF, 2-methyl THF, 1,4-dioxane, MTBE, DME, diglyme, t-butanol, and t-amyl alcohol. A particular solvent is THF. The base utilized in both steps may be added at the start of the first. Examples of suitable bases include potassium t-butoxide, sodium t-butoxide, potassium t-amylate, sodium t-amylate, sodium hexamethydisilazide, potassium hexamethyldisilazide, lithium diisopropylamide, n-butyl lithium, sec-butyl lithium, and t-butyl lithium. A particular base is potassium t-butoxide.

In some embodiments of the invention, the neutralization of Compound D-benzoate is carried out at a temperature of from about −50° C. to about 50° C. (e.g., from about 15° C. to about 25° C.) for about 0.5 hours to about 24 hours (e.g., for about 3 hours to about 5 hours.) In some embodiments, Compound H is contacted with Compound D in the presence of a base at a temperature of from about −50° C. to about 50° C. (e.g., from about 0° C. to about 25° C.) for about 2 hours to about 5 hours.

From about 1.8 to about 3 molar equivalents (e.g., from about 2.5 to 3 molar equivalents) of the base is used relative to Compound H and from about 1 to about 1.5 molar equivalents (e.g., about 1.2 molar equivalents) of Compound D-benzoate is used relative to Compound H.

Compound D-benzoate can be prepared as shown below:

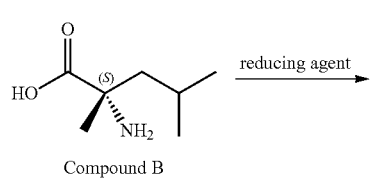

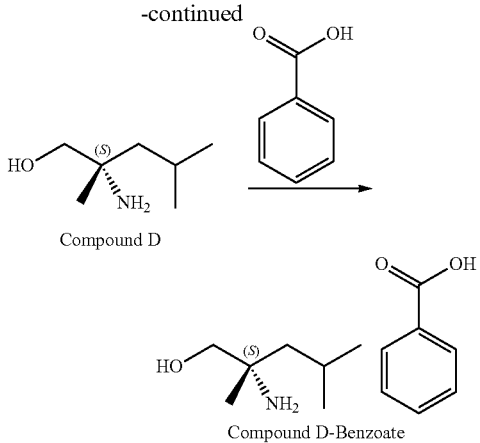

wherein Compound B is contacted with a reducing agent under conditions sufficient to form Compound D, which is contacted with benzoic acid under conditions sufficient to form Compound D-benzoate.

Examples of reducing agents include $NaBH_4/BF_3 \cdot Et_2$, $NaBH_4/I_2$, $NaBH_4/TMSCl$, $NaBH_4/H_2SO_4$, $NaBH_4/MsOH$, $NaBH_4/TsOH$, $NaBH_4/HCl$, $NaBH_4/AlCl_3$, $CDI/NaBH_4$, $BH_3THF$ complex, $BH_3$ dimethyl sulfide complex, diborane, $LiAlH_4$ and $Li/AlCl_3/t$-BuOH. In some embodiments of the invention, the reducing agent is $NaBH_4/BF_3 \cdot Et_2O$. The amount of the reducing agent can be from about 0.5 to about 4 molar equivalents (e.g., about 2 molar equivalents) relative to Compound B.

The reduction of Compound B is typically carried out in a solvent such as THF, 2-Me-THF, THF, 2-methyl THF, 1,4-dioxane, MTBE, DME and diglyme, or mixtures thereof. A preferred solvent is THF. In some embodiments, the concentration of Compound B in the solvent is from about 2% to about 25%. The reduction may be carried out at a temperature of from about −50° C. to about 50° C. (e.g., from about 0° C. to about 25° C.) for about 0.5 hours to about 24 hours (e.g., about 5 hours to about 8 hours.)

According to the approach shown above, Compound D is contacted with benzoic acid in a solvent such as MTBE, MTBE/heptane, THF, THF/heptane, EtOAc, EtOAc/heptane, IPAc, IPAc/heptane, EtOH, EtOH/heptane, IPA, IPA/heptane, toluene, and acetonitrile. A preferred solvent is MTBE. In some embodiments of this invention, this reaction is carried out at a temperature of from about 0° C. to about 60° C. (e.g., from about 45° C. to about 50° C.) for about 1 to 2 hours. In some embodiments, from about 0.8 to about 1.5 molar equivalents of benzoic acid is utilized relative to Compound D (e.g., about 1.1 molar equivalents). In some embodiments, the concentration of Compound D in the solvent is from about 2% to about 25%.

Another intermediate useful in the large-scale synthesis of Compound J and pharmaceutically acceptable salts thereof is Compound H, which can be prepared as shown below:

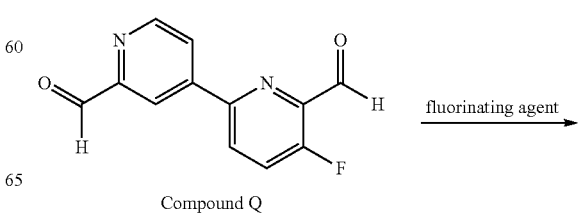

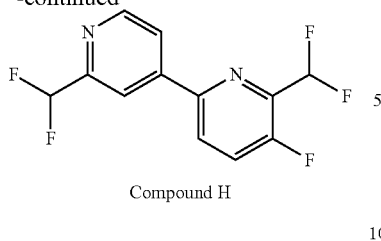

Compound H

In this approach, Compound H is prepared by contacting Compound Q with a fluorinating agent under conditions sufficient to form Compound H. Examples of fluorinating agents include $SF_4$, $PhSF_3$, $R_2NSF_3$ (DAST, Morph-DAST), dialkylamidodifluorosulfinium tetrafluoroborate ($[R_2N=SF_2]$ (XtalFluor-E®, XtalFluor-M®)$BF_4$), Deoxo-Fluor (BAST), Selectfluor™, and 4-tert-butyl-2,6-dimethylphenylsulfur trifluoride. A preferred fluorinating agent is DAST. Depending on the particular agent used, from about 1 to about 5 molar equivalents (e.g., about 3.5) of the fluorinating agent is used relative to Compound Q.

Compound Q is preferably contacted with the fluorinating agent in a solvent such as methylene chloride, chloroform, $CCl_4$ and toluene. A preferred solvent is methylene chloride. The concentration of Compound Q in the solvent may vary from about 2% to about 25%. The reaction typically occurs at a temperature of from about −20° C. to about 60° C. (e.g., from about 0° C. to about 25° C.) for about 1 hour to about 100 hours (e.g., from about 24 hours to about 30 hours.)

Compound Q can be prepared from Compound L4 as shown below:

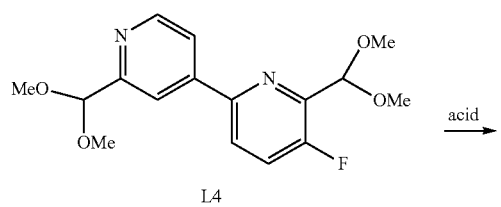

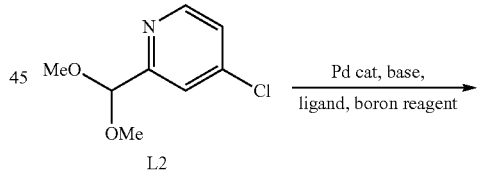

Q

In this approach, Compound Q is prepared by contacting Compound L4 or a salt thereof (e.g., the phosphoric acid salt L4-phosphate) with an acid under conditions sufficient to form Compound Q. Examples of suitable acids include HCl, HBr, HI, $H_2SO_4$, $H_3PO_4$, $HNO_3$, MsOH, TsOH and $HBF_4$. A preferred acid is hydrochloric acid.

Reaction with the acid is preferably carried out in a solvent such as water or DMSO/water (a preferred solvent is water) and at a temperature of from about 0° C. to about 100° C. (e.g., from about 55° C. to about 60° C.). The reaction is typically carried out for about 1 hour to about 24 hours (e.g., two hours). The concentration of Compound L4 can be varied to optimize yield, and may be, for example, from about 2 to about 25%. In some embodiments of the invention, from about 1 to about 10 molar equivalents (e.g., 5 molar equivalents) of the acid is utilized relative to Compound L4.

A particularly useful salt of Compound L4 is L4-phosphate, which can be prepared as shown below:

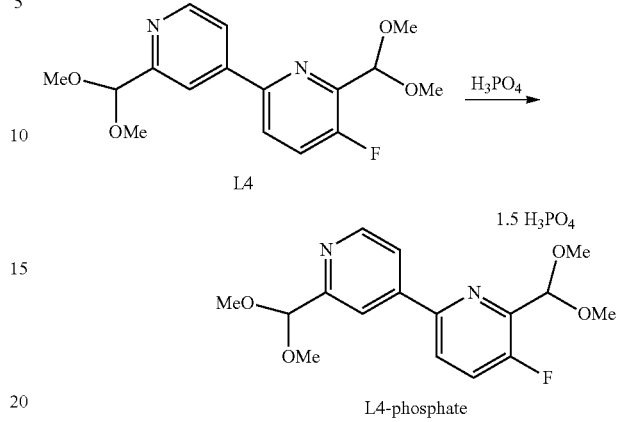

In this approach, Compound L4 is contacted with phosphoric acid under conditions sufficient to prepare Compound L4-phosphate. The reaction can be carried out in solvents such as MeOH, EtOH, IPA, EtOAc, IPAc, MTBE, THF, 2-Me-THF, toluene, heptane, or mixtures thereof. A preferred solvent system is toluene/methanol/heptane.

The reaction is typically run at a temperature of from about 0° C. to about 60° C. (e.g., about 15° C. to about 45° C.) for about 1 hour to about 24 hours (e.g., about 10 hours to about 12 hours). In some embodiments of the invention, from about 1 to about 2 (e.g., about 1.6) molar equivalents of the phosphoric acid is utilized relative to Compound L4. The concentration of Compound L4 in the solvent can range from about 2% to about 25%.

Compound L4 can be prepared using the approach shown below:

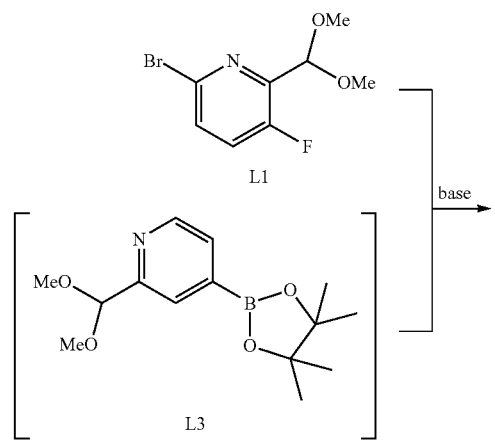

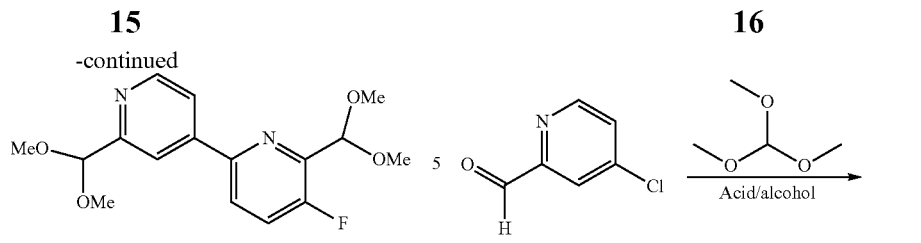

L4

Here, Compound L2 is contacted with a palladium catalyst, base, ligand, and boron reagent under conditions sufficient to form Compound L3, which is contacted with Compound L1 in the presence of a catalyst and a base under conditions sufficient to form Compound L4.

The preparation of Compound L3 is typically done in a solvent such as THF, 2-MeTHF, 1,4-dioxane, DME, MTBE, Et$_2$O, or ACN. In some embodiments, the solvent is 2-MeTHF. Examples of palladium catalysts that may be used to prepare Compound L3 include Pd(OAc)$_2$, PdCl$_2$(dppf), Pd(PPh$_3$)$_4$, PdCl$_2$(PPh$_3$)$_2$, and Pd$_2$(dba)$_3$. A preferred catalyst is Pd$_2$(dba)$_3$. Bases useful in the formation of Compound L3 include NaOAc, KOAc, NaHCO$_3$, KHCO$_3$, Na$_2$CO$_3$, K$_2$CO$_3$, K$_2$HPO$_4$, and K$_3$PO$_4$. A preferred base is KOAc. Suitable ligands include PCy$_3$, SPhos and Xphos. A preferred ligand is Xphos. Boron reagents useful in the reaction include tetrahydrodiboron, PinBH and Pin$_2$B$_2$. A preferred boron reagent is Pin$_2$B$_2$.

In some embodiments of the invention, Compound L2 is contacted with the palladium catalyst, base, ligand, and boron reagent at a temperature of from about 0° C. to about 100° C. (e.g., from about 70° C. to about 80° C.) for about 0.5 hours to about 48 hours (e.g., about 16 hours to about 24 hours.) In some embodiments, from about 0.8 to about 2 (e.g., 1) molar equivalents of the boron reagent is utilized relative to Compound L$_2$. In some embodiments, the concentration of Compound L$_2$ in the solvent is from about 2% to about 25%.

The next step of the reaction shown above, wherein Compound L3 is reacted with Compound L1, is typically carried out in a solvent such as water, THF, 2-MeTHF, 1,4-dioxane, DME, MTBE, Et$_2$, and mixtures thereof. A preferred solvent is water/2-MeTHF. The concentration of Compound L1 can range from about 2% to about 25%, but like the conditions for all of the reactions disclosed herein, these numbers can be varied using means well known to those skilled in the art to maximize product yield and minimize cost.

Examples of bases that can be used for the formation of Compound L4 include Na$_2$CO$_3$, K$_2$CO$_3$, Na$_3$PO$_4$, K$_3$PO$_4$, NaOH and KOH. A preferred base is sodium carbonate (Na$_2$CO$_3$). Depending on the base, about 1 to 2 molar equivalents (e.g., 2 molar equivalents) of base are used relative to Compound L2. This step is carried out at a temperature of from about 20° C. to about 100° C. (e.g., from about 70° C. to about 80° C.) for about 1 hours to about 48 hours (e.g., about 16 hours to about 24 hours). From about 1 to about 2 molar equivalents (e.g., 1 equivalent) of Compound L1 is used relative to Compound L2.

The synthetic intermediate Compound L2 can be prepared as shown below:

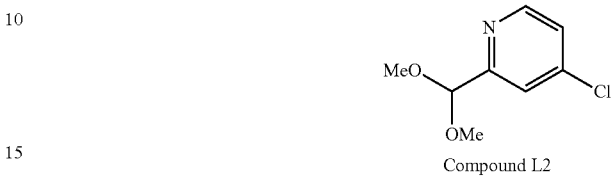

SM3

Compound L2

In this approach, the compound SM3 is contacted with trimethoxymethane in the presence of an acid under conditions sufficient to form the Compound L2. Examples of suitable acids include H$_2$SO$_4$, MsOH, TsOH, H$_3$PO$_4$, HNO$_3$, HCl, and HBr. A preferred acid is hydrochloric acid.

The reaction shown above is typically conducted in a solvent such as 1,4-dioxane, DME, Et$_2$O, THF, 2-Me-THF, toluene, DCM, MTBE, ACN, methanol. A preferred solvent is methanol. The temperature at which this reaction is conducted can range from about 0° C. to about 80° C. (e.g., from about 60° C. to about 65° C.), and its duration can range from about 0.5 hours to about 48 hours (e.g., about 6 to about 10 hours).

In some embodiments of the invention, from about 0.01 to about 1 molar equivalents (e.g., about 0.2 molar equivalents) of the acid is utilized relative to SM$_3$, and from about 1 to about 4 molar equivalents (e.g., about 2 molar equivalents) of trimethoxymethane are used relative to SM3. The concentration of SM3 in the solvent can range from about 2% to about 30%.

Compound L2 may also be prepared as shown below using reaction conditions similar to those described above (albeit with more trimethoxymethane):

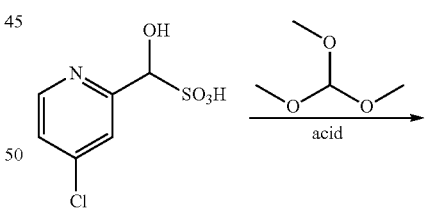

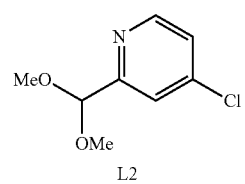

L2

The synthetic intermediate Compound L1 can be prepared as shown below:

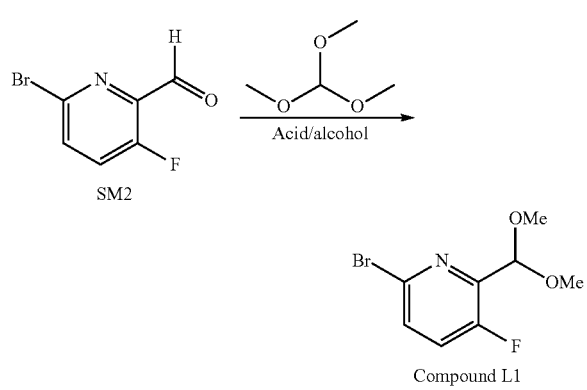

In this approach, Compound L1 is prepared by contacting Compound SM2 with trimethoxymethane in the presence of an acid under conditions sufficient to form the acetal Compound L1. Examples of suitable acids include $H_2SO_4$, MsOH, TsOH, $H_3PO_4$, $HNO_3$, HCl, and HBr. A preferred acid is hydrochloric acid.

This reaction is preferably conducted in a solvent such as 1,4-dioxane, DME, $Et_2O$, THF, 2-Me-THF, toluene, DCM, MTBE, ACN and methanol. A preferred solvent is methanol.

In some embodiments of the invention, SM2 is contacted with trimethoxymethane in the presence of the acid at a temperature of from about 0° C. to about 80° C. (e.g., from about 60° C. to about 65° C.) for about 0.5 hours to about 48 hours (e.g., about 3 hours to about 6 hours). From about 0.01 to about 1 molar equivalents (e.g., about 0.05 molar equivalents) of the acid is typically utilized relative to SM2. From about 1 to about 4 molar equivalents (e.g., about 2 molar equivalents) of trimethoxymethane is typically used relative to SM2. In some embodiments, the concentration of SM2 in the solvent is from about 2% to about 30%.

In one embodiment of the invention, Compounds J, K, and S are prepared as shown in Scheme 1:

Scheme 1

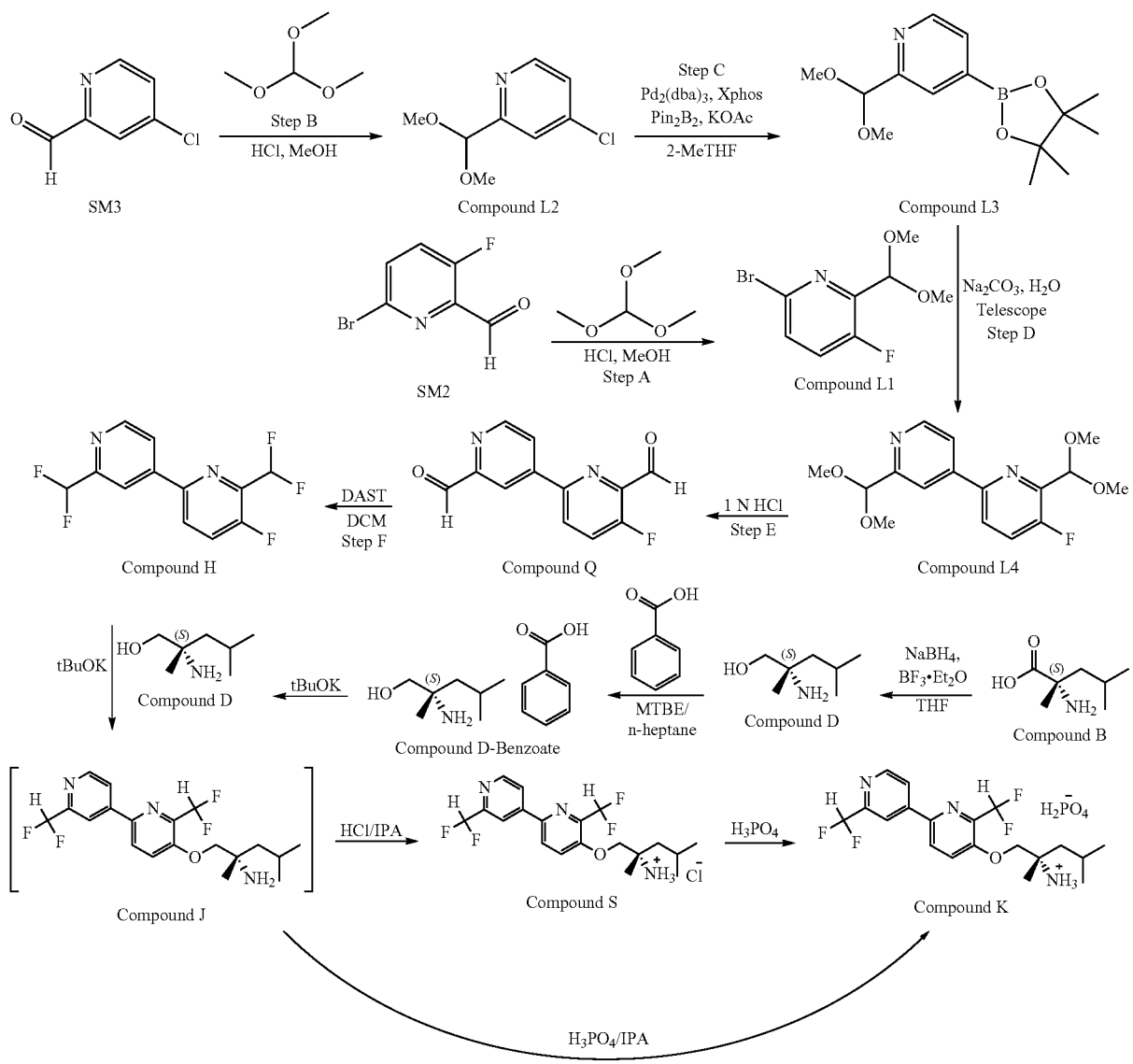

In this approach, Compound J or a pharmaceutically acceptable salt thereof is prepared by a process comprising: a) contacting Compound L3 with Compound L1 in the presence of a catalyst and base under conditions sufficient to form Compound L4; b) contacting Compound L4, or a salt thereof, with an acid under conditions sufficient to form Compound Q; c) contacting Compound Q with a fluorinating agent under conditions sufficient to form Compound H; and d) contacting compound H with Compound D in the presence of a base under conditions sufficient to form said Compound J.

Compound S is prepared by a process comprising exposing Compound J to hydrochloric acid in a solvent.

Compound K is prepared by a process comprising: a) neutralizing Compound S with a base under conditions sufficient to form Compound J; and b) exposing the resulting Compound J to phosphoric acid in a solvent under conditions sufficient to form Compound K.

In a specific embodiment of the invention, Compound K is prepared by a process comprising: a) contacting Compound L3 with Compound L1 in the presence of a catalyst and a base under conditions sufficient to form Compound L4; b) contacting Compound L4 with an acid under conditions sufficient to form Compound Q; c) contacting Compound Q with a fluorinating agent under conditions sufficient to form Compound H; d) contacting Compound H with Compound D in the presence of a base under conditions sufficient to form Compound J; e) contacting Compound J to hydrochloric acid in a solvent under conditions sufficient to form Compound S; f) neutralizing Compound S with a base under conditions sufficient to form Compound J; and g) exposing the resulting Compound J to phosphoric acid in a solvent under conditions sufficient to form Compound K.

In another embodiment, Compound K is prepared by a process comprising: a) contacting Compound L3 with Compound L1 in the presence of a catalyst and base under conditions sufficient to form Compound L4; b) contacting L4 with an acid under conditions sufficient to form Compound Q; c) contacting Compound Q with a fluorinating agent under conditions sufficient to form Compound H; d) contacting compound H with Compound D in the presence of a base under conditions sufficient to form Compound J; e) exposing the resulting Compound J to phosphoric acid in a solvent under conditions sufficient to form said Compound K.

This invention encompasses methods of ensuring that the final active pharmaceutical ingredient has a purity suitable for administration to human patients. To this end, potential impurities including those shown below in Table 1 were synthesized and characterized by $^1$H NMR and mass spectroscopy.

TABLE 1

| Impurity No. | Compound |
|---|---|
| 1 | 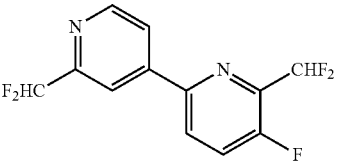 [SMILES: Fc1ccc(-c2ccnc(C(F)F)c2)nc1C(F)F]<br>2',6-bis(difluoromethyl)-5-fluoro-2,4'-bipyridine |
| 2 | 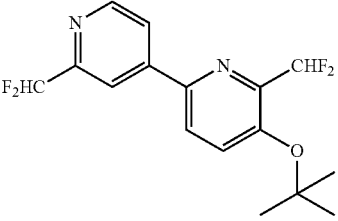 [SMILES: CC(C)(C)Oc1ccc(-c2ccnc(C(F)F)c2)nc1C(F)F]<br>5-(tert-butoxy)-2',6-bis(difluoromethyl)-2,4'-bipyridine |
| 3 | 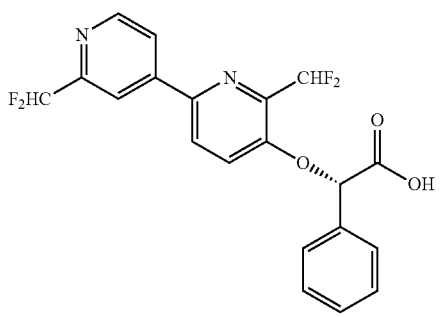 [SMILES: O=C(O)[C@@H](Oc1ccc(-c2ccnc(C(F)F)c2)nc1C(F)F)c1ccccc1]<br>(S)-2-((2',6-bis(difluoromethyl)-[2,4'-bipyridin]-5-yl)oxy)-2-phenylacetic acid |

TABLE 1-continued

| Impurity No. | Compound |
|---|---|
| 4 | 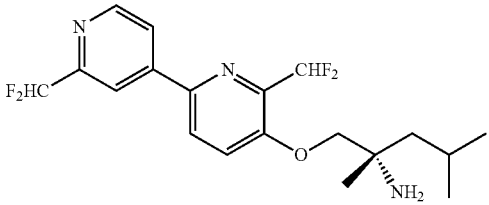 [SMILES: CC(C)C[C@](C)(N)COc1ccc(-c2ccnc(C(F)F)c2)nc1C(F)F]
(S)-1-((2',6-bis(difluoromethyl)-[2,4'-bipyridin]-5-yl)oxy)-2,4-dimethylpentan-2-amine |
| 5 | 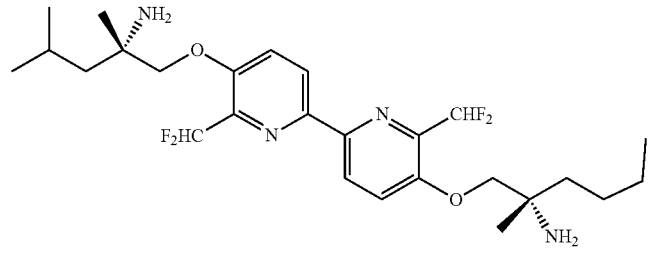 [SMILES: CCCC[C@](C)(N)COc1ccc(-c2ccc(OC[C@@](C)(N)CC(C)C)c(C(F)F)n2)nc1C(F)F]
(S)-1-((5'-(((S)-2-amino-2,4-dimethylpentyl)oxy)-6,6'-bis(difluoromethyl)-[2,2'-bipyridin]-5-yl)oxy)-2-methylhexan-2-amine |

The compounds in Table 1 were observed at various stages of the lab-scale development work that led to methods of the invention.

This invention comprises a method of testing the purity of Compound J or a pharmaceutically acceptable salt thereof by testing for the presence of one or more of the compounds listed in Table 1. A preferred method comprises testing for the presence of the one or more compounds using mass spectroscopy and/or HPLC.

5.1 EXAMPLES

Various embodiments of the invention may be understood by considering the examples provided below. In these examples, unless otherwise indicated, all temperatures are set forth in degrees Celsius and all parts and percentages are by weight. Reagents may be purchased from commercial suppliers and were used without further purification unless otherwise indicated. (Reagents may also be prepared following standard literature procedures known to those skilled in the art.)

Unless otherwise specified, reactions were run at ambient temperature (or room temperature.) Reactions were typically assayed by HPLC and terminated as judged by the consumption of starting material.

Compound structures and purities were confirmed by one or more of the following methods: proton nuclear magnetic resonance ($^1$H NMR) spectroscopy, $^{13}$C NMR spectroscopy, mass spectroscopy, infrared spectroscopy, melting point, X-ray crystallography, LC-MS and/or HPLC. Chemical shifts are reported in parts per million (ppm, δ) downfield from a standard, e.g., an internal standard, such as TMS. Alternatively, $^1$H NMR chemical shifts were referenced to signals from residual protons in deuterated solvents as known in the art. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

5.1.1 Synthesis of
6-bromo-2-(dimethoxymethyl)-3-fluoropyridine
(Compound L1)

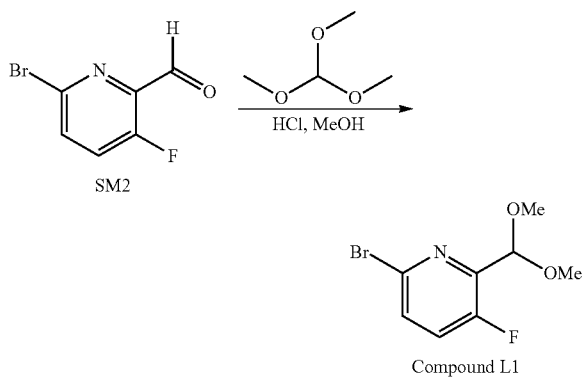

A solution of HCl/MeOH (10 mL of 3.9 M solution, 0.05 eq.) was charged into a mixture of SM2 (158.5 g, 777 mmol, 1 eq.), MeOH (1585 mL, 10V) and trimethoxymethane (166 g, 15.6 mol, 2.0 eq.). The resulting mixture was aged at 60-65° C. (reflux) until reaction completions (3-6 h) and then cooled to 10-20° C. After being concentrated to 2-3V below 50° C. and diluted with 2-Me-THF (10V), the reaction was quenched with 10% $K_2CO_3$ (3V). The organic layer was separated and concentrated to 1-2V below 50° C. It was flushed with 2-Me-THF (5V) and then diluted with more 2-Me-THF (5V) to give a solution of Compound L1 in 2-Me-THF (845.2 g, 99% purity, 21.7% assay, 94.4% solution yield). LC-MS: m/z 250, 252, 220, 218 (M-OMe) $^1$H NMR (400 MHz, CHLOROFORM-d) δ 7.38 (dd, J=3.5, 8.6 Hz, 1H), 7.17-7.30 (m, 1H), 5.37-5.48 (m, 1H), 3.39 (s, 6H).

5.1.2 Synthesis of 4-chloro-2-(dimethoxymethyl)pyridine (Compound L2)

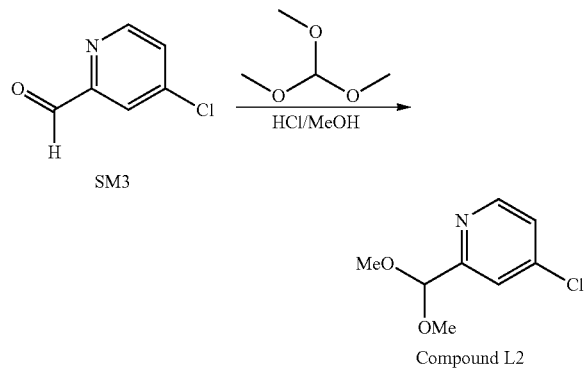

HCl/MeOH (42.3 mL 3.9 M solution, 0.20 eq.) was charged into a mixture of SM3 (117.3 g, 819.5 mmol, 1 eq.), MeOH (1160 mL, 10V) and trimethoxymethane (174 g, 1.64 mol, 2.0 eq.). The mixture was heated to 60-65° C. (reflux) until reaction completion (6-10 h) and then cooled to 10-20° C. After being concentrated to 3-5V and diluted with 2-Me-THF (10V), the reaction was quenched with 10% $K_2CO_3$ (3V, pH 8-9). The organic layer was separated and concentrated to 1-2V, flushed with 2-Me-THF (5V×2), and then diluted with 2-Me-THF (5V) to give a solution of Compound L2 in 2-Me-THF (588.5 g, 99.18% purity by HPLC, 22.3% assay, 85.3% solution yield). $^1$H NMR (400 MHz, CHLOROFORM-d) δ 8.42-8.57 (m, 1H), 7.56 (d, J=2.0 Hz, 1H), 7.25 (dd, J=2.1, 5.3 Hz, 1H), 5.28-5.39 (m, 1H), 3.38 (s, 6H). LC-MS m/z 187, 156 (M-OMe).

5.1.3 Synthesis of 2',6-bis(dimethymethyl)-5-fluoro-2,4'-bipyridine phosphate (Compound L4-phosphate)

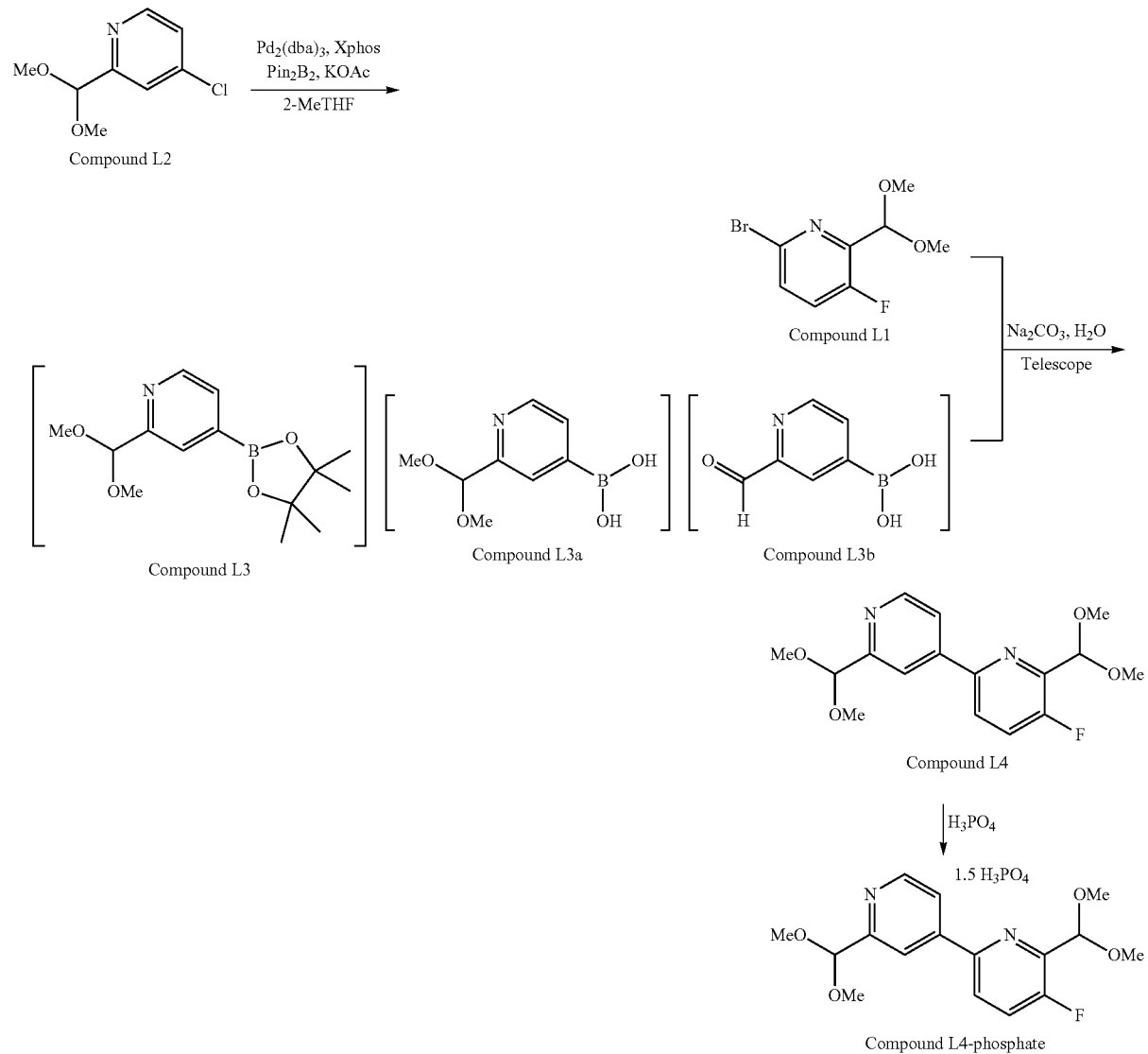

Preparation of L3: A mixture of compound L2 in 2-Me-THF (95.5 g, 1.00 eq., 5-6V), 2-Me-THF (10V), Pin₂B₂ (1.05 eq.), KOAc (3.0 eq.) and Xphos (0.02 eq.) was degassed by sparging with N₂. Pd₂(dba)₃ (0.01 eq.) was added, and the mixture degassed by sparging with N₂ again. The reaction mixture was heated to 70-80° C. and stirred until the borylation of L2 was complete (16-24 h) to give L3, which was used directly for the next Suzuki coupling step.

Preparation of L4 via Suzuki coupling of L3 and L1: After cooling to 15-25° C., a solution of compound L1 in 2-Me-THF (0.96 eq., 5-6V), Na₂CO₃ (2.0 eq. solid) and H₂O (5V) were added sequentially. After degassing by sparging with N₂, the reaction mixture was aged at 70-80° C. until the Suzuki coupling was complete (16-24 h). After cooling to 15-25° C., the reaction mixture was filtered through a pad of diatomite (0.5×) and the filter-cake was rinsed with 2-Me-THF (1-2V). The organic layer in the filtrate was separated, concentrated to 1-2V, diluted with toluene (10V) and washed with L-cysteine/NaOH (pH>10)(5×, ratio of L-cysteine/NaOH/H₂O: 1/0.5/9) twice. The organic layer was then washed with H₂O (5×) and concentrated to 5V to give a toluene solution of Compound L4 free base in toluene. An analytical sample of L4 free base was obtained by crystallization in heptane/MTBE. ¹H NMR (400 MHz, chloroform-d) δ 8.66-8.77 (m, 1H), 8.06 (d, J=1.22 Hz, 1H), 7.94 (dd, J=1.77, 5.20 Hz, 1H), 7.86 (dd, J=3.55, 8.56 Hz, 1H), 7.51-7.60 (m, 1H), 5.63 (s, 1H), 5.44-5.48 (m, 1H), 3.54-3.60 (m, 6H), 3.43-3.49 (m, 6H); mp 41.8° C. (DSC peak); XRPD 2θ: 6.70, 7.61, 9.67, 13.56, 13.77, 13.99, 15.36, 19.36, 20.71, 21.81, 23.10, 26.96, 27.72, 28.02, 29.36, 31.88, 32.04, 39.09.

Preparation of L4 phosphate: A solution of 85% H₃PO₄ (1.6 eq. based on Compound L4 free base) in MeOH (1-2V) was added over 2 h to the above L4 solution in toluene to afford a suspension. The suspension was concentrated to 3V below 45° C. and n-heptane (10V) was added over 2 h. The mixture was concentrated to 10V below 45° C. and the batch temperature was adjusted to 15-25° C. After stirring for 6-8 h, the mixture was filtered, and the filter-cake rinsed with n-heptane (1-2V). The wet cake was dried with a slight N₂ sweep under reduced pressure at 40° C. to give 190.5 g of L4-Phosphate (93.2% yield). ¹H NMR (400 MHz, DMSO-d₆) δ 8.63-8.72 (m, 1H), 8.24 (dd, J=3.6, 8.7 Hz, 1H), 8.11 (d, J=1.1 Hz, 1H), 8.01 (dd, J=1.8, 5.2 Hz, 1H), 7.92 (dd, J=8.7, 9.9 Hz, 1H), 5.58 (s, 1H), 5.36 (s, 1H), 3.43 (s, 6H), 3.35 (s, 6H). LC-MS: [M+H]⁺ 323.2; mp. 124.2° C. (DSC peak); XRPD 2θ: 4.87, 7.35, 9.20, 12.76, 14.66, 15.06, 15.92, 16.99, 19.56, 19.81, 20.26, 21.55, 22.12, 23.09, 23.39, 23.73, 25.61, 26.25, 27.48, 27.73, 28.26, 29.55, 30.35, 31.10, 31.82, 34.13, 34.68, 36.04, 39.48.

5.1.4 Synthesis of 5-fluoro-[2,4'-bipyridine]-2',6-dicarbaldehyde (Compound Q)

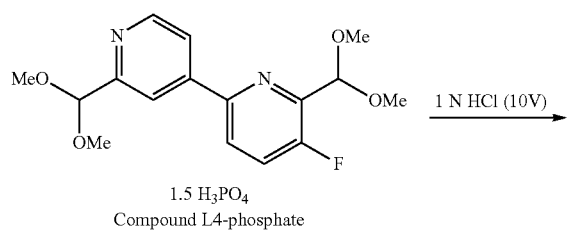

Compound L4-phosphate

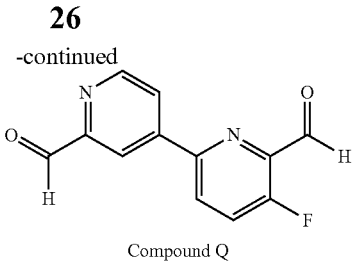

Compound Q

A mixture of compound L4-Phosphate (177 g, 111 g L4 free base=1.0×), 1N HCl (1110 mL, 10V) and toluene (555 mL, 5V) was stirred at 15-25° C. for 0.5-1.0 h. The organic phase was separated off and the aqueous layer was stirred at 55-60° C. for 2 h. The mixture was slowly (3 h) concentrated to remove generated MeOH under reduced pressure (−0.08 to −0.085 Mpa) at 55-60° C. and then cooled to 30-40° C. DCM (777V) was charged and the pH of the mixture was adjusted to 5-7 with 15% Na₂CO₃ (3.5-4.5×). The layers were separated, and the aqueous layer was extracted with DCM (2V). The combined organic layer was washed with H₂O (5V) and filtered through a pad of Na₂SO₄ (1×). The filter-pad was rinsed with DCM (2V) and the combined filtrate concentrated to 8-10V. The reactor wall was spray washed with 2V DCM and then n-heptane (8-10V) was charged over 2.0-5.0 h. The mixture was concentrated to 10-12V below 60° C. under normal atmospheric pressure (residual DCM in supernatant 40%). The suspension was aged at 30-40° C. for 1.0-2.0 h, 5-10° C. for 6-8 h and filtered. The filter-cake was washed with 1:4 DCM/n-heptane (1-2V) and dried under reduced pressure at 40-50° C. to give 80.19 g Compound Q (98% yield). LC-MS: [M+H]⁺ 231; [M+H+H₂O]⁺ 249; ¹H NMR (400 MHz, CHLOROFORM-d) δ 10.27 (s, 1H), 10.18 (s, 1H), 8.91-9.00 (m, 1H), 8.51-8.59 (m, 1H), 8.24-8.31 (m, 1H), 8.17 (dd, J=3.5, 8.7 Hz, 1H), 7.77 (t, J=9.0 Hz, 1H); mp. 150° C. (DSC peak).

5.1.5 Synthesis of 2',6-bis(difluoromethyl)-5-fluoro-2,4'-bipyridine (Compound H)

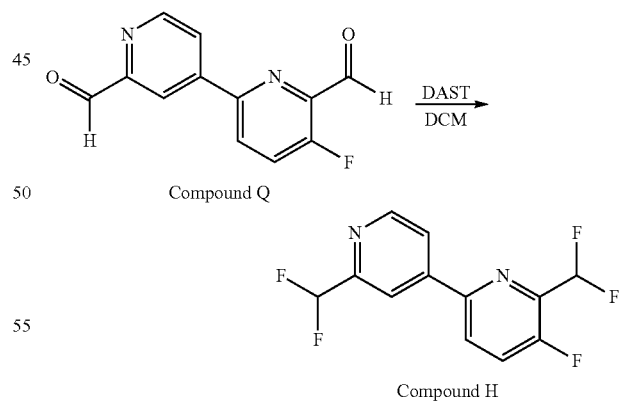

A solution of compound Q (30.0 g, 1.00×) and Et₃N (0.044×) in dry DCM (KF≤0.02%, 20×) was cooled to 0-5° C. DAST (3.50×) was slowly added at 0-10° C. and the mixture was then aged at 20-25° C. until reaction completion (~24 h). The reaction mixture was quenched into 15% K₂CO₃ (28×) at 0-20° C. for two hours and aged at 20-25° C. for 0.5 h. The organic layer was separated, cooled to 10-20° C. and treated with 1 M HCl (9.9-11.1×) at 10-25° C.

for 0.5-1 h. After settling for 0.5 h, the mixture was filtered through a pad of Diatomite earth (~0.5×) followed by a small rinse DCM (2.0-3.0×). The filtrate was settled, and the organic layer was separated, washed with $H_2O$ (10×) and filtered through a pad of silica gel (~1.5×). The silica pad was washed with DCM (5.0×-6.0× three times) until the purity of Compound H in the filtrate fraction decreased <90%. The combined filtrate was concentrated to ~2-3V below 30° C. and then co-distilled with isopropanol 50° C. until residual DCM<5.0% (6-7× total IPA used) with a final volume of 3-4V. The distillation residue was aged at 55-60° C. for 0.5 h, cooled to 35-40° C., aged for 0.5 h. Water (9.0-10.0×) was slowly added at 33-40° C. (1-3 h) and the mixture stirred for 0.5 h. After aging at 15-20° C., the suspension was filtered and the filter-cake washed sequentially with IPA/$H_2O$ (1:4, w/w, 1×), $H_2O$ (2×). The wet-cake was dried under reduced pressure at 40-45° C. until KF<0.3% and residual IPA<0.1% (18-24 h) to give 30.15 g compound H (82% yield). Melting point (mp) 75° C. (DSC peak). LC-MS: $[M+H]^+$ 275.2; $^1$H NMR (400 MHz, CHLOROFORM-d) δ 8.71-8.89 (m, 1H), 8.22 (s, 1H), 7.91-8.12 (m, 2H), 7.71 (t, J=8.9 Hz, 1H), 7.00 (s, 1H), 6.87 (s, 1H), 6.82-7.05 (m, 1H), 6.59 (s, 1H), 6.73 (s, 1H).

5.1.6 Synthesis of (S)-2-amino-2,4-dimethylpentan-1-ol benzoate (Compound D-Benzoate)

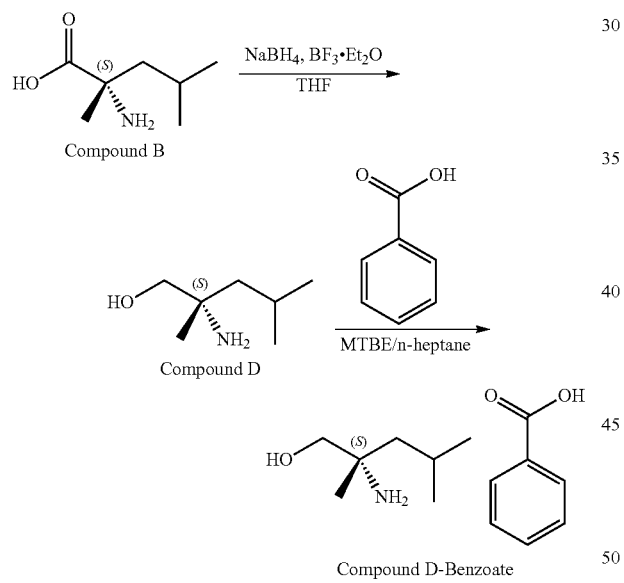

$BF_3·Et_2O$ (200 g, 2.0 equiv) was slowly added to a mixture of $NaBH_4$ (53 g, 2.0 equiv) in THF (1.0 L) at 0-10° C. The reaction mixture was warmed to 15 C and then (S)-(α)methylleucine (100 g, 1.0 equiv) was added over 1 h at <25° C. The mixture was aged at 20-25° C. for 5-8 hours and slowly quenched into 10% aq. NaOH (750 mL) at 25-30° C. The organic layer was separated, washed with 15% aq. NaCl (200 mL) and then diluted with n-heptane (300 mL). 2N HCl (~300 mL) was added to the mixture until the pH reached 1-2. The organic layer was separated and extracted with 1 N HCl (300 mL). The combined aqueous layer was basified with 30% NaOH (~500 mL) until pH>13 and then extracted with MTBE (500 mL×3). The combined organic extract was dried over anhydrous $Na_2SO_4$ (100-200 g), filtered, concentrated to ~200 mL, and then flushed with MTBE (200-500 mL) until moisture content in the concentrate was <0.5%. The solution of the amino alcohol D was then slowly (5 h) added to a solution of benzoic acid (93 g, 1.1 equiv) in MTBE (500 mL) at 45-50° C. After stirring for 1 h, the mixture was slowly (5-8 h) cooled to 20-25° C. and aged for 5-8 h to give a suspension. The suspension was filtered, the filter-cake washed with 1/1 MTBE/n-heptane (150 mL) and dried at 40-50° C. under reduced pressure to give Compound D-benzoate in 92% yield. mp. 125.4° C. (DSC peak); $^1$H NMR (400 MHz, METHANOL-$d_4$) δ 7.88-7.99 (m, 2H), 7.27-7.46 (m, 3H), 3.45-3.62 (m, 2H), 1.69-1.87 (m, 1H), 1.56-1.66 (m, 1H), 1.44-1.54 (m, 1H), 1.29 (s, 3H), 1.00 (d, J=6.60 Hz, 6H); XRPD 2θ: 6.67, 6.83, 12.84, 13.37, 15.16, 16.95, 17.83, 19.90, 20.32, 21.23, 22.28, 23.70, 24.09, 24.42, 26.24, 26.91, 27.49, 30.60, 32.64, 33.98, 34.98, 35.13.

5.1.7 Synthesis of (S)-1-((2',6-bis(difluoromethyl)-[2,4'-bipyridin]-5-yl)oxy)-2,4-dimethylpentan-2-amine hydrochloride (Compound S)

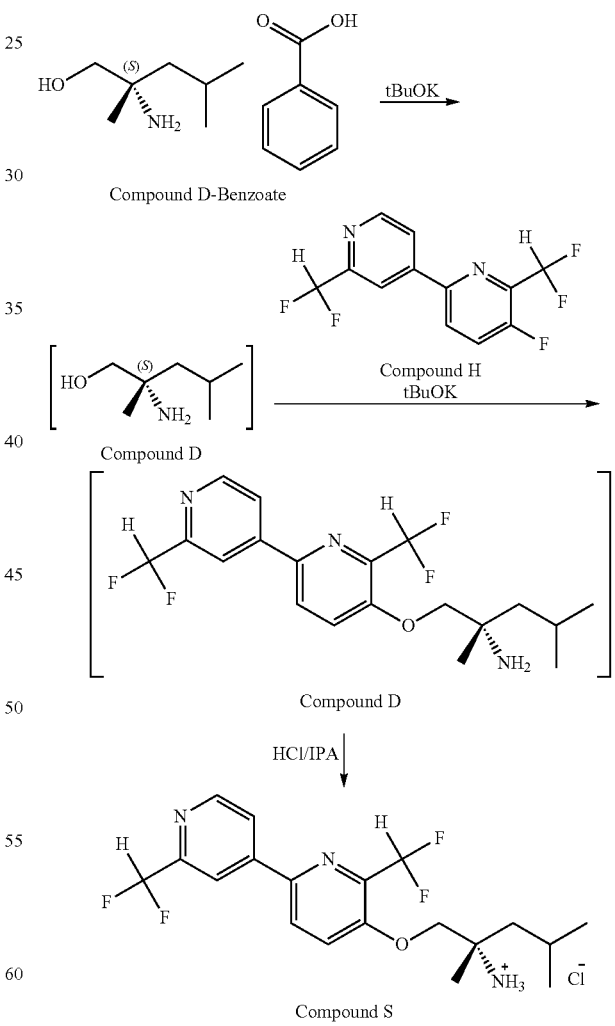

Solid t-BuOK (2.5-3.0 eq. based on Compound H) was charged in portions to a mixture of Compound D-benzoate (1.2 eq. based on Compound H) and THF (10.5-11.6×) at 15-20° C. The mixture was warmed to 20-25° C., stirred for 3-5 h and then cooled to 0-5° C. A solution of compound H (1.00×) in THF (3.6-4.5×) was slowly (~1 h) added while maintaining the batch temperature below 20° C. The reaction mixture was aged at 20-25° C. until reaction completion (1-3 h). MTBE (6×) was added, and the mixture cooled to 10-15° C. $H_2O$ (9.0-11.0×) was added slowly (1-3 h) while keeping the batch temperature below 25° C. The layers were separated, and the aqueous layer was extracted with MTBE (2.2×). The combined organic layer was concentrated to 2-3V under reduced at below 30° C. Free base compound J: $^1$H NMR (400 MHz, DMSO-$d_6$) δ 8.70-8.84 (m, 1H), 8.40 (d, J=8.8 Hz, 1H), 8.33 (s, 1H), 8.22 (br d, J=5.0 Hz, 1H), 7.81 (d, J=8.8 Hz, 1H), 7.17-7.41 (m, 1H), 6.89-7.13 (m, 1H), 3.82-3.95 (m, 2H), 1.74-1.88 (m, 1H), 1.55 (br s, 2H), 1.33-1.46 (m, 2H), 1.12 (s, 3H), 0.93 (t, J=7.1 Hz, 6H). After solvent swap to IPA by co-distillation (6.0-6.5×) to 2-3V, more IPA (3.8-4.2×) was added and the mixture heated to 50-60° C. A solution of 35% HCl (0.44-0.47×) in IPA (1.3-1.5×) was added slowly (~1 h) while keeping the batch at 50-60° C. The resulting suspension was aged at 50-60° C. for 1.0-2.0 h, cooled to 20-30° C. in 2.0-4.0 h, stirred at 20-30° C. for 1.0-2.0 h and then filtered. The filter-cake was washed with MTBE (3.5-4.0×) and dried under reduced pressure at 40-50° C. for 16-24 h to give Compound S. LC-MS m/z 386.1; mp. 246.4° C. (DSC peak), $^1$H NMR (400 MHz, DMSO-d6) δ 8.81 (d, J=5.3 Hz, 1H), 8.51 (br s, 2H), 8.45 (d, J=8.9 Hz, 1H), 8.34 (s, 1H), 8.24 (d, J=5.1 Hz, 1H), 7.91 (d, J=8.9 Hz, 1H), 7.56-7.87 (m, 1H), 6.90-7.23 (m, 1H), 4.29 (s, 2H), 1.72-1.91 (m, 2H), 1.54-1.72 (m, 1H), 1.42 (s, 3H), 0.86-1.00 (m, 6H).

5.1.8 Synthesis of (S)-1-((2',6-bis(difluoromethyl)-[2,4'-bipyridin]-5-yl)oxy)-2,4-dimethylpentan-2-amine phosphate (Compound K)

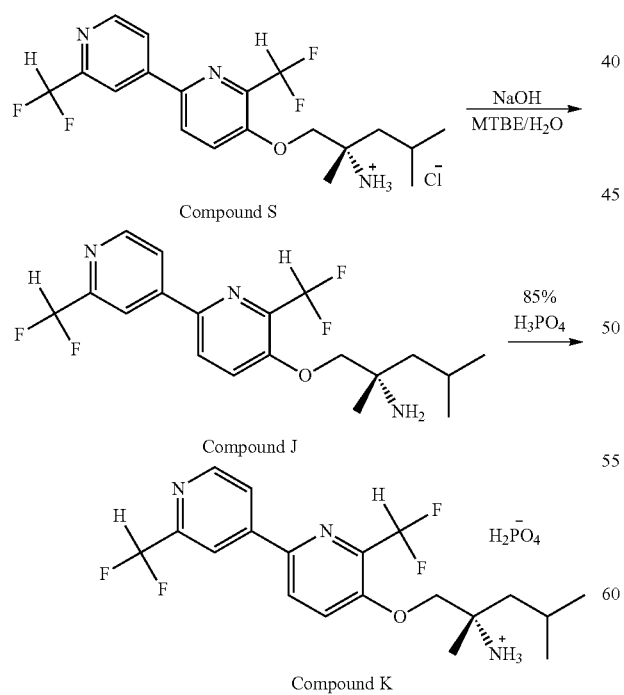

A mixture of compound S (9.5 kg, 1.0×), MTBE (76.0 kg, 8.0×), water (50.0 kg, 5.3×) was treated with 20% aqueous NaOH (0.95 kg NaOH solid in 4.0 kg water) at 35-40° C. until all solid dissolved (2.0-5.0 h). The reaction mixture was cooled to 20-25° C. and stirred for 1.0-2.0 h. The organic layer was separated, washed with water (46.5 kg, 4.9×) and concentrated to ~25 L (2-3×) at ≤30° C. under reduced pressure. After solvent swap to IPA by co-distillation under reduced pressure ≤50° C. (79.0 kg IPA, 8.3×) with a final volume of 29-38 L (3-4×), the distillation residue was diluted with IPA (60 kg) and heated to 50-60° C. A solution of $H_3PO_4$ (2.8 kg, 0.29×) in IPA (5.0 kg, 0.53×) was added over 2.0-4.0 h. More IPA (22.0 kg, 2.3×) was added and the batch was stirred for 2.0-4.0 h at 50-60° C. The batch was cooled to 15-20° C. over 2.0-4.0 h and then stirred for 1.0-2.0 h at 15-20° C. The resulting suspension was filtered, and the filter cake washed sequentially with IPA (27.0 kg, 2.84×) and MTBE (31 kg, 3.3×). The wet-cake was dried at 45-55° C. for 17-24 h under reduced pressure to give compound K. The salt ratio between Compound J and phosphoric acid in Compound K was determined to be 1:1 (two separate HPLC methods using a UV and an IC detector, respectively). The purity of Compound K was 98.7-99.9 area % by HPLC. The crystallinity of Compound K was confirmed by XRPD and further supported by DSC. $^1$H NMR (400 MHz, DMSO-$d_6$) δ 8.78 (d, J=5.1 Hz, 1H), 8.41 (d, J=8.8 Hz, 1H), 8.31 (s, 1H), 8.21 (d, J=5.1 Hz, 1H), 7.88 (brd, H), 7.47 (t, $J_{H-C-F}$=54 Hz, 1H), 7.04 (t, $J_{H-C-F}$=54 Hz, 1H), 4.03-4.29 (m, 2H), 1.72-1.87 (m, 1H), 1.60-1.69 (m, 1H), 1.49-1.59 (m, 1H), 1.33 (s, 3H), 0.92 (d, J=6.6, 3H), 0.87 (d, J=6.6, 3H); $^{13}$C NMR (100 MHz, DMSO-d6) δ 21.62, 22.74, 24.61, 24.82, 44.69, 54.57, 72.80, 110.53 (t, $J_{C-F}$=237 Hz), 113.84 (t, $J_{C-F}$=238 Hz), 116.68, 122.19, 125.03, 140.07 (t, $J_{C-F}$=22 Hz), 144.13, 145.98, 150.52, 152.80 (t, $J_{C-F}$=25 Hz), 153.51. XRPD: 4.80, 5.99, 7.43, 7.88, 9.57, 11.58, 14.84, 15.21, 15.75, 17.91, 18.83, 19.17, 20.41, 20.84, 21.67, 23.23, 23.95, 24.41, 24.72, 25.27, 26.37, 30.14.

5.1.9 Synthesis of (S)-1-((2',6-bis(difluoromethyl)-[2,4'-bipyridin]-5-yl)oxy)-2,4-dimethylpentan-2-amine phosphate (Compound K)

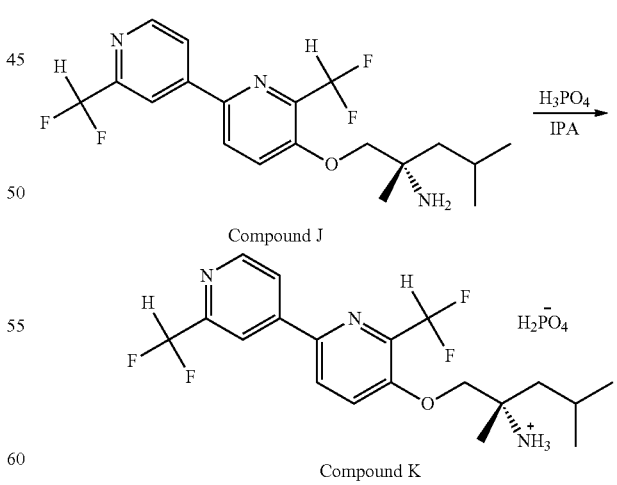

To a solution of Compound J (9.14 g) in IPA (100 mL) was added Compound K seed (0.18 g) at 50-60° C. A solution of 85% phosphoric acid (2.87 g, 1.05 equiv) in IPA (7 mL) was added over a period of 2-4 h. The suspension was aged for 2-4 h, cooled to 15-20° C. over 2-4 h and aged for 1-2 h. The suspension was filtered, and the filter cake washed with IPA (20 mL) followed by MTBE (44 mL). The wet cake was dried under reduced pressure at 45-55° C. for 17-24 h to give 11.3 g of Compound K, 98% yield.

Compound K seed formation: IPA (1.0 mL) was added to Compound J (50.08 mg, 0134 mmol, 1.0 eq.) to form a clear solution at ambient temperature and then phosphoric acid (0.156 mL, 1M in IPA, 0.156 mmol, 1.20 eq.) was added. The mixture was stirred for 6 h to give a suspension and then aged at 60° C. for 30 min. After cooling to room temperature, heptane (0.5 mL) was added, and the resulting mixture stirred for 1 h. The resulting suspension was filtered, and the filter-cake was washed with MTBE (0.5 mL), dried at 45-48° C. under reduced pressure overnight to afford Compound K seed (59.28 mg, 94.4% yield).

The salt ratio, purity, XRPD, DSC and TGA data are substantially identical to the data obtained for Compound K in Example 2.

Each reference (e.g., patents, patent applications, and publications) cited herein is incorporated herein by reference in its entirety.

What is claimed is:

1. A method of preparing(S)-1-((2',6-bis(difluoromethyl)-[2,4'-bipyridin]-5-yl)oxy)-2,4-dimethylpentan-2-amine (Compound J):

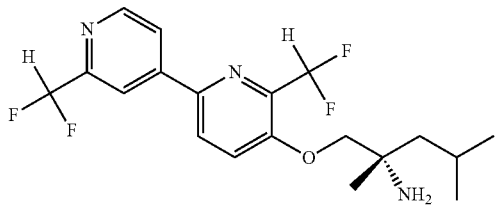

J which comprises contacting Compound H:

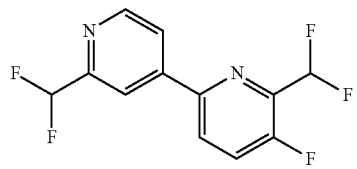

H with Compound D:

D or a salt thereof in the presence of a base under conditions sufficient to form Compound J.

2. The method of claim 1, wherein the base is an alkoxide.

3. The method of claim 2, wherein the alkoxide is potassium tert-butoxide.

4. The method of claim 3, wherein Compound H is prepared by contacting Compound Q:

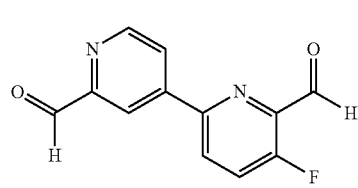

Q with a fluorinating agent under conditions sufficient to form Compound H.

5. The method of claim 4, wherein the fluorinating agent is DAST.

6. The method of claim 5, wherein Compound Q is prepared by contacting Compound P:

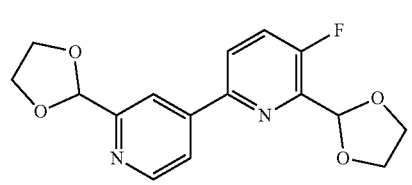

P with an acid under conditions sufficient to form Compound Q.

7. The method of claim 6, wherein the acid is hydrochloric acid.

8. The method of claim 7, wherein Compound P is prepared by contacting Compound L:

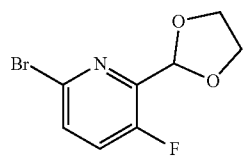

L with Compound N:

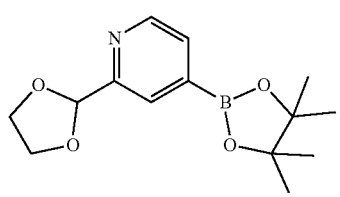

N under conditions sufficient to form Compound P.

9. The method of claim 5, wherein Compound Q is prepared by contacting Compound L4:

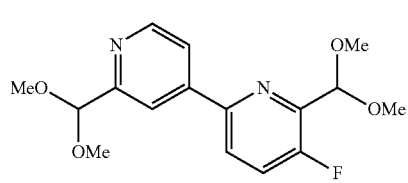

with an acid under conditions sufficient to form Compound Q.

10. The method of claim 9, wherein the acid is hydrochloric acid.

11. The method of claim 10, wherein Compound L4 is prepared by contacting Compound L3:

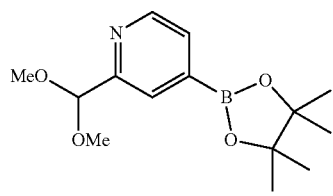

with Compound L1:

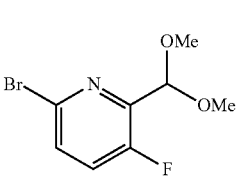

in the presence of a catalyst, ligand, and base under conditions sufficient to form Compound L4.

12. The method of claim 11, wherein the catalyst is Pd2(dba)2.

13. The method of claim 12, wherein the ligand is Xphos.

14. The method of claim 11, wherein the base is sodium carbonate.

15. The method claim 1, wherein the salt of Compound D is a benzoate salt.

16. The method of claim 13, wherein the solvent is isopropyl alcohol.

* * * * *